(12) United States Patent
Jensen et al.

(10) Patent No.: US 7,932,024 B2
(45) Date of Patent: *Apr. 26, 2011

(54) METHOD, CHIP, DEVICE AND SYSTEM FOR COLLECTION OF BIOLOGICAL PARTICLES

(75) Inventors: Gert Bolander Jensen, Copenhagen (DK); Lars Thomsen, Ålborg (DK); Oene Robert Veltman, Ålborg (DK)

(73) Assignee: Delta, Dansk Elektronik, Lys & Akustik, Hørsholm (DK)

( * ) Notice: Subject to any disclaimer, the term of this patent is extended or adjusted under 35 U.S.C. 154(b) by 178 days.

This patent is subject to a terminal disclaimer.

(21) Appl. No.: 10/590,768

(22) PCT Filed: Feb. 25, 2005

(86) PCT No.: PCT/DK2005/000133
§ 371 (c)(1),
(2), (4) Date: Nov. 16, 2007

(87) PCT Pub. No.: WO2005/083391
PCT Pub. Date: Sep. 9, 2005

(65) Prior Publication Data
US 2008/0190219 A1    Aug. 14, 2008

(30) Foreign Application Priority Data
Feb. 26, 2004   (DK) ................. 2004 00306

(51) Int. Cl.
C12Q 1/00  (2006.01)
C12Q 1/68  (2006.01)
(52) U.S. Cl. ................ 435/6; 435/4
(58) Field of Classification Search ........... None
See application file for complete search history.

(56) References Cited

U.S. PATENT DOCUMENTS

| | | | |
|---|---|---|---|
| 342,548 A | 5/1886 | Walker |
| 895,729 A | 8/1908 | Cottrell |
| 1,204,907 A | 11/1916 | Schmidt |
| 1,250,088 A | 12/1917 | Burns |
| 1,605,648 A | 11/1926 | Cooke |
| 1,931,436 A | 10/1933 | Deutsch |
| 2,085,349 A | 6/1937 | Wintermute |
| 2,129,783 A | 9/1938 | Penney |
| 2,142,129 A | 1/1939 | Hoss et al. |
| 2,297,601 A | 9/1942 | Williams |
| 2,847,082 A | 8/1958 | Roos |
| 3,910,779 A | 10/1975 | Penney |
| 3,999,964 A | 12/1976 | Carr |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 4,970,154 A | 11/1990 | Chang |
| 5,674,742 A | 10/1997 | Northrup et al. |
| 5,723,591 A | 3/1998 | Livak et al. |
| 5,891,694 A | 4/1999 | Arisawa et al. |
| 5,989,824 A * | 11/1999 | Birmingham et al. ............ 435/6 |
| 6,126,800 A | 10/2000 | Caillat et al. |
| 6,364,941 B2 | 4/2002 | Liu et al. |
| 6,511,831 B1 | 1/2003 | Bernhagen et al. |
| 6,586,253 B1 | 7/2003 | Harrison et al. |
| 6,623,544 B1 | 9/2003 | Kaura |
| 6,673,621 B1 | 1/2004 | Mitchell |
| 2001/0029793 A1 | 10/2001 | Moler et al. |
| 2002/0017195 A1 | 2/2002 | Tolvanen |
| 2002/0115201 A1 | 8/2002 | Barenburg et al. |
| 2003/0136205 A1 | 7/2003 | Totoki |
| 2003/0146100 A1 | 8/2003 | Huang et al. |

FOREIGN PATENT DOCUMENTS

| | | |
|---|---|---|
| DE | 27 56 164 A1 | 6/1979 |
| DE | 2756164 A1 | 6/1979 |
| EP | 1481083 B1 | 12/2004 |
| GB | 2329633 A | 3/1999 |
| WO | WO8903426 A2 | 4/1989 |
| WO | WO9708293 A1 | 3/1997 |
| WO | WO9928742 A1 | 6/1999 |
| WO | WO9938612 A1 | 8/1999 |
| WO | WO9957314 A1 | 11/1999 |
| WO | WO0026405 A1 | 5/2000 |
| WO | WO0119963 A2 | 3/2001 |
| WO | WO 03/004996 A2 | 1/2003 |
| WO | WO 03/031067 A1 | 4/2003 |
| WO | WO03074731 A2 | 9/2003 |
| WO | WO2004/009840 A1 | 1/2004 |
| WO | WO 2004/013329 A1 | 2/2004 |

OTHER PUBLICATIONS

Atrih, et al. 2001. Analysis of the role of bacterial endospore cortex structure in resistance properties and demonstration of its conservation amongst species. *Journal of Applied Microbiology*, 91:364-372.
Boe, et al. 1989. Replication origins of single-stranded-DNA plasmid pUB110. *Journal of Bacteriology*, 171(6):3366-3372.

(Continued)

*Primary Examiner* — Young J Kim
(74) *Attorney, Agent, or Firm* — Peter B. Schull; K. Kalan; Berenbaum Weinshienk PC

(57) ABSTRACT

The present invention relates to a method, a chip, a device, and a system for collection of biological particles. The method makes use of electrostatic attraction of biological particles to charged electrodes and preferably operates with gaseous samples. The method, chip, device, and system are e.g. useful for collecting pathogenic biological particles, such as bacterial spores and vira, from air samples and allow for subsequent analysis of the collected biological particles.

12 Claims, 8 Drawing Sheets

OTHER PUBLICATIONS

Cano, et al. 1995. Revival and identification of bacterial spores in 25- to 40-million-year-old Dominican amber. *Science*, 268:1060-1064.

Chen, et al. 2000. Analysis of DNA fragments by microchip electrophoresis fabricated on poly(methyl methacrylate) substrates using a wire-imprinting method. *Electrophoresis*, 21:165-170.

Cho, et al. 1999. Kinetics of inactivation of *Bacillus subtilis* spores by continuous or intermittent Ohmic and conventional heating. *Biotechnology and Bioengineering*, 62(3):368-372.

Cserhalmi, et al. 2002. Inactivation of *Saccharomyces cerevisiae* and *Bacillus cereus* by pulsed electric fields technology. *Innovative Food Science & Emerging Technologies*, 3:41-45.

Daniel, et al. 1998. Silicon microchambers for DNA amplification. *Sensors and Actuators A*, 71:81-88.

Dull, et al. 2002. *Bacillus anthracis* aerosolization associated with a contaminated mail sorting machine. *Emerging Infectious Diseases*, 8(10):1044-1047.

Fridez, et al. 1996. PCR DNA typing of stamps: Evaluation of the DNA extraction. *Forensic Science International*, 78:103-110.

Grahl, et al. 1996. Killing of microorganisms by pulsed electric fields. *Appl. Microbiol. Biotechnol.*, 45:148-157.

Johns, et al. 1994. Improved methods for the detection of *Bacillus anthracis* spores by the polymerase chain reaction. *Letters in Applied Microbiology*, 18:236-238.

Johnson, et al. 2001. Development of a fully integrated analysis system for ions based on ion-selective optodes and centrifugal microfluidics. *Anal.Chem.*, 73:3940-3946.

Kopp, et al. 1998. Chemical amplication: Continuous-flow PCR on a chip. *Science*, 280:1046-1048.

Lado, et al. 2002. Alternative food-preservation technologies: Efficacy and mechanisms. *Microbes and Infection*, 4:433-440.

Lagally, et al. 2001. Single-molecule DNA amplification and analysis in an integrated microfluidic device. *Analytical Chemistry*, 73:565-570.

Levi, et al. 2003. Molecular detection of anthrax spores on animal fibres. *Letters in Applied Microbiology*, 36:418-422.

Mafart, et al. 1997. Modelling the heat stress and the recovery of bacterial spores. *International Journal of Food Microbiology*, 37:131-135.

Mainelis, et al. 1999. Collection of airborne microorganisms by electrostatic precipitation. *Aerosol Science and Technology*, 30:127-144.

Mainelis, et al. 2002a. Collection of airborne microorganisms by a new electrostatic precipitator. *Journal of Aerosol Science*, 33:1417-1432.

Mainelis, et al. 2002b. Design and collection efficiency of a new electrostatic precipitator for bioaerosol collection. *Aerosol Science & Technology*, 36(11):1073-1085.

Mainelis, et al. 2002c. Effect of electrical charges and fields on injury and viability of airborne bacteria. *Biotechnology and Bioengineering*, 79(2):229-241.

Mainelis, et al. 2003. Application of electrostatic precipitation for simultaneous determination of culturable and total airborne microorganisms. *American Society for Microbiology General Meeting*, Meeting Abstract, May 18-22, 2003.

O'Brien, et al. Size and concentration measurement of an industrial aerosol. *Am. Ind. Hyg. Assoc. J.*, 47(7):386-392, 1986.

Northrup, et al. 1998. A miniature analytical instrument for nucleic acids based in micromachined silicon reaction chambers. *Analytical Chemistry*, 70(5):918-922.

Pugmire, et al. 2002. Surface characterization of laser-ablated polymers used for microfluidics. *Analytical Chemistry*, 74(4):871-878.

Schafer, et al. 2003. Rapid detection and determination of the aerodynamic size range of airborne mycobacteria associated with whirlpools. *Applied Occupational and Environmental Hygiene*, 18(1):41-50.

Schneegaβ, et al. 2001. Miniaturized flow-through PCR with different template types in a silicon chip thermocycler. *Lab on a Chip*, 1:42-49.

Shoffner, et al. 1996. Chip PCR. I. Surface passivation of microfabricated silicon-glass chips for PCR. *Nucleic Acids Research*, 24(2):375-379.

Spilimbergo, et al. 2003. Inactivation of bacteria and spores by pulse electric field and high pressure $CO_2$ at low temperature. *Biotechnology and Bioengineering*, 82(1):118-125.

Sung, et al. 2001. Plastic microchip electrophoresis for genetic screening: The analysis of polymerase chain reactions products of fragile X (CGG)n alleles. *Electrophoresis*, 22:1188-1193.

Tsong, T. Y. 1991. Electroporation of cell membranes. *Biophysical Journal*, 60:297-306.

Tsong, et al. 1999. Biological effects of electric shock and heat denaturation and oxidation of molecules, membranes, and cellular functions. *Annals New York Academy of Sciences*, 888:211-232.

Vincent, et al. 1999. Application of recent advances in aerosol sampling science towards the development of improved sampling devices: The way ahead. *J. Environ. Monit.*, 1:285-292.

International Search Report dated Aug. 17, 2005 for PCT/DK2005/000133.

Co-pending U.S. Appl. No. 10/590,630, filed Aug. 23, 2006, titled Method, Chip, Device and System for Extraction of Biological Materials.

Co-pending U.S. Appl. No. 10/590,632, filed Aug. 23, 2006, titled Method, Chip, Device and Integrated System for Detection Biological Particles.

Co-pending U.S. Appl. No. 10/590,648, filed Aug. 23, 2006, titled Method, Kit and System for Enhanced Nested PCR.

Brown, K. L. 1994. Spore resistance and ultra heat treatment processes. *Journal of Applied Bacteriology Symposium Supplement*, 76:67S-80S.

Lee, et al. 1987. Electrical injury mechanisms: Electrical breakdown of cell membranes. *Plastic and Reconstructive Surgery*, 80(5):672-679.

Riley, R. L. 1974. Airborne infection. *The American Journal of Medicine*, 57:466-475.

Mainelis, G. et al.; "Collection of Airborne Microorganisms by Electrostatic Precipitation"; Aerosol Science and Technology; vol. 30:2; pp. 127-144; Feb. 1999; American Association for Aerosol Research.

International Search Report dated Jun. 14, 2005 for PCT/DK2005/000132.

International Preliminary Report on Patentability dated Feb. 6, 2006 for PCT/DK2005/000132.

International Search Report dated Aug. 19, 2005 for PCT/DK2005/000130.

International Preliminary Report on Patentability dated Mar. 20, 2006 for PCT/DK2005/000130.

Huang, Ying et al.; MEMS-Based Sample Preparation for Molecular Diagnostics; Anal Bioanal Chem; 2002; pp. 49-65, vol. 372; Springer-Verlag.

Lee, Sang-Wook et al.; A Micro Cell Lysis Device; Sensors and Actuators; 1999; pp. 74-79, vol. 73; Elsevier Science S.A.

Cheng, Jing et al.; Isolation of Cultured Cervical Carcinoma Cells Mixed with Peripheral Blood Cells on a Bioelectronic Chip; Anal Chem; 1998; pp. 2321-2326, vol. 70; American Chemical Society.

Pappaert, K., et al.; Diffusion-Reaction Modelling of DNA Hybridization Kinetics on Biochips; Chemical Engineering Science; 2003; pp. 4921-4930, vol. 58; Elsevier Ltd.

* cited by examiner

METHOD, CHIP, DEVICE AND SYSTEM FOR COLLECTION OF BIOLOGICAL PARTICLES

CROSS REFERENCE TO RELATED APPLICATION

This application is a U.S. National Phase of PCT International Application Number PCT/DK2005/000133, filed on Feb. 25, 2005, designating the United States of America and published in the English language, which claims priority under 35 U.S.C. §119 to Denmark Application Number PA 2004 00306 filed on Feb. 26, 2004. The disclosures of the above-described applications are hereby incorporated by reference in their entirety.

FIELD OF THE INVENTION

The present invention relates to a method, a chip, a device and a system for collection of biological particles. The method makes use of electrostatic attraction of biological particles to charged electrodes and preferably operates with gaseous samples.

BACKGROUND

In order to facilitate rapid detection of airborne pathogens that are capable of causing either natural or deliberate epidemics, it is of utmost importance to collect particles containing biological material directly from air in a form suitable for further analysis. Typically, particles containing or consisting of one or more biological organisms (bioparticles), are captured by passing (samples of) air through porous filters. To size fractionate for selected ranges of particles, a succession of filters have been used to select for the right size particles, which are subsequently collected at—and can be cultured on growth media plates within the collecting device (The Andersen sampler).

When bioparticles contain live organisms or spores, they can give rise to growth (colonies) on the media plate, which subsequently can be collected and analyzed easily. However, the researcher will have to wait for the colonies (colony forming units or CFU) to become visible, which, depending on the cultured organism, can take from days to weeks. Additionally, the possibility exists that a biological organism of interest might not thrive on the growth media. It is also possible that particles of interest are captured within or adhere to the filtering system and therefore go un-detected.

To compensate for sample loss a large volume of air need to be processed through the system. A complimentary method, which can be used in the combination with filter sampling, is to maximize the number of particles in a given volume of air, by using e.g. cyclones or other vortex type gaseous samplers that facilitate an initial concentration of particles. The later technique has also been used to concentrate particles into a volume of liquid, giving immediate access to captured bioparticles for a variety of different microbiological, biochemical, and molecular analyses.

Funnelling particles into a liquid is associated with heating and evaporation of the liquid and often volumes of liquid (larger than 1 ml) are required to prevent the system from drying out during the capture process. Subsequently, the liquid can be processed by centrifugation to perform a final concentrate of the sample.

Sampling of bioparticles can be done by air to air, air to surface or air to liquid methods. Liquid methods can be cumbersome because of freezing effects at temperatures below 0° C. Key aspects of the sampling are sampling volume, capture efficiency, and the concentrating efficiency of the sampling technology. A standard cyclone is capable of taking in one $m^3$ of air per second and concentrating captured particles in 1-2 ml of fluid, which is a large volume in biochemical analyses. A volume in this range would fill a 96 well plate and consume reagents equivalent to approximately C 14 per plate per second. It is obvious that the rapid air sampling by the cyclone quickly is compromised by the subsequent sample preparation.

In one approach, electrostatic precipitation of airborne biological particles was utilized for sampling of bacteria onto agar plates in conventional macro scale devices (Mainelis et al 2002a; Mainelis et al 2002b) and for decontamination of a dental practice (Iversen & Tolo 1975).

SUMMARY OF THE INVENTION

An object of the present invention relates to the provision of methods, chips, devices and systems for direct collection of biological particles from gaseous samples such as air samples.

Another object of the present invention relates to the provision of methods, chips, devices and systems for up-concentrating biological particles from a large gaseous sample into a much smaller volume, i.e. increasing the concentration of the biological particles.

Yet another object of the present invention relates to the provision of methods, chips, devices and systems in which collection and up-concentration of the biological particles are performed in the same structure and preferably also in the same step.

Still another object of the present invention relates to the provision of methods, chips, devices and systems that easily allows for further analysis of collected biological particles.

A further object of the present invention relates to the provision of methods, chips, devices and systems that easily allows for further analysis of collected biological particles.

Also, an object of the invention relates to the provision of methods, chips, devices and systems that collect biological particles with high capture efficiency.

Other objects of the invention will become apparent when reading the description and the examples.

The present invention relates to a method, a chip, a device and a system that allow for large volumes of air to be processed, without submitting the collected sample to either a media or a liquid, in order to maximize the yield and minimize the number of concomitant steps to perform the optimization of the sample collection into a concentrate. The invention describes a biological collection system which may involve electrostatic particle collection, e.g. performed in a microstructure, i.e. a chip, that allows for flows of up to several hundred mL air per minute. The present invention allows for capturing biological particles with very high efficiency and in a format that is highly suitable for various subsequent analyses.

The present invention an important implication of the invention is that biological particles now can be concentrated from e.g. an air sample. This is an important finding since the currently used liquid-based microsystem, i.e. chips or biochips, by nature are only capable of handling liquid sample sizes in the microliter range. Therefore, Microsystems are not suitable for handling liquid samples harvested from e.g. a cyclone producing 1-2 ml/s. According to the present invention, microsystems are now are useful as bioaerosol sampling technology, if the sampling of biological particles is done directly in the microsystem.

An aspect of the present invention relates to a method for collecting a biological particle from air, the method comprising the steps of:
1) providing a sample chamber and a first and a second electrode, the first and the second electrode and the sample chamber being so positioned that at least a part of the sample chamber is between the first and the second electrode,
2) providing an gaseous sample in the sample chamber,
3) applying an electrical field between the first and second electrodes to assist electrostatic collection, in the sample chamber, of a biological particle in the gaseous sample.

In a preferred embodiment of the invention, the method furthermore comprises a step 4) of contacting the biological particle collected in the sample chamber with a first liquid reagent.

In a preferred embodiment of the invention, the method furthermore comprises a step 5) of subjecting the collected biological particle to further analysis. Thus, in this embodiment the method is not only for collecting biological particles, but also for analysis and/or . . . .

Another aspect of the present invention related to a chip for collection of biological particles, the chip comprising a sample chamber comprising:
a sample chamber with a first opening in fluid connection with the surrounding air and a second opening to form a fluid connection with a device, the sample chamber comprising an gaseous sample,
a first and a second electrode positioned at opposing sides of the sample chamber.

A further aspect of the invention relates to a device for collecting biological particles in a chip. The device may for example be an air-sampling device or a device for collecting biological particles from a gaseous sample. The device preferably comprises:
a chip site where the chip is to be located in order be functionally associated with the device, and
a programmable unit comprising a software that effects that the device performs one or more actions selected from the group consisting of:
applying an first potential to the first electrode and a second potential to the second electrode, thus resulting in a potential difference and an electric field between the first and second electrode, to assist electrostatic collection, in the sample chamber, of a biological particle from the gaseous sample,
contacting collected biological particles in the sample chamber with a first liquid reagent, and
performing further analysis of the collected biological particles.

Still a further aspect of the invention relates to a system for collecting biological particles, the system comprising a chip as defined herein functionally associated with a device as defined herein.

BRIEF DESCRIPTION OF THE FIGURES

In the following some embodiments of the present invention will be described with reference to the figures, wherein
FIG. 3 shows a sample chamber comprising two plate or sheet-like electrodes,
FIG. 4 shows a cross section of a sample chamber.

DETAILED DESCRIPTION OF THE INVENTION

Figure 1:
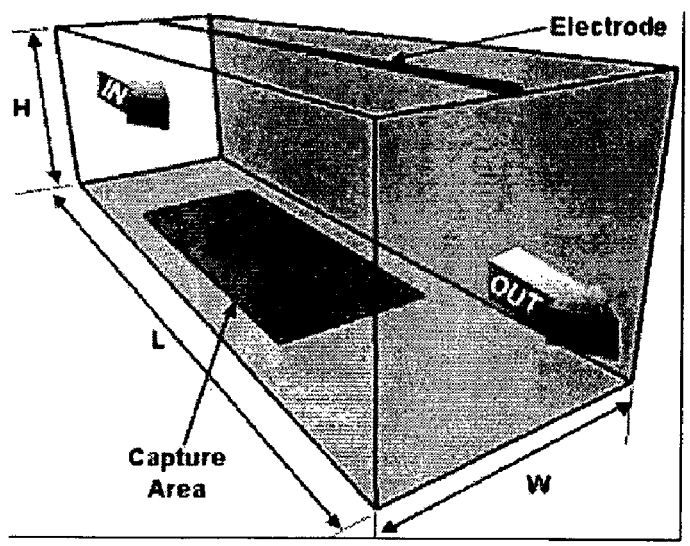
FIG. 1 illustrates a sample chamber comprising a plate or sheet-like electrode and four point electrode.

An aspect of the present invention relates to method for collecting a biological particle from air, the method comprising the steps of:
1) providing a sample chamber and a first and a second electrode, the first and the second electrode and the sample chamber being so positioned that at least a part of the sample chamber is between the first and the second electrode,
2) providing an gaseous sample in the sample chamber,
3) applying an electrical field between the first and second electrodes to assist electrostatic collection, in the sample chamber, of a biological particle in the gaseous sample.

In an embodiment of the invention, the method furthermore comprises a step of terminating a gas flow, e.g. the gas flow used for providing the gaseous sample.

In a preferred embodiment of the invention, the method furthermore comprises a step 4) of contacting the biological particle collected in the sample chamber with a first liquid reagent.

In a preferred embodiment of the invention, the method furthermore comprises a step 5) of subjecting the collected biological particle to further analysis. Thus, in this embodiment the method is not only for collecting biological particles, but also for analysis and/or detection.

The method may thus comprise step 1), 2) and 3), such as:
steps 1), 2), 3), and 4); or
steps 1), 2), 3), and 5); or
steps 1), 2), 3), 4), and 5).

According to the present invention, the phrase "collecting a biological particle" relates to collecting the particle in the sample chamber, that is to say, retaining the biological particle in the sample chamber, so that when the gaseous sample is replaced by a fluid, the biological particles remain in sample chamber. Typically the collection is performed by the electrostatic forces of the electric field acting on the biological particles.

The term "and/or" used in the context "X and/or Y" should be interpreted as "X", or "Y", or "X and Y".

According to the present invention, the term "biological particle" relates to related to a particle comprising e.g. a microorganism and/or a virus and/or a fragment thereof.

The term "gaseous sample" relates to a sample comprising one or more gasses and possibly also biological particles. The gaseous sample may e.g. be a gaseous sample, such as environmental samples of air, sample of air resulting from a vacuum suction of powdered materials like earth, sand, dust or unidentified powder. The gaseous sample to be examined may originate from a person exhaling a breath sample containing or susceptible to contain microorganisms.

According to the present invention the terms "sample chamber", "container" and "reaction chamber" are used interchangeably.

In a preferred embodiment of the invention, the sample chamber is comprised by a chip, that is to say, a cartridge or a biochip. The sample chamber may e.g. be comprised by a chip as defined herein.

In a preferred embodiment of the invention, the sample chamber is comprised by a chip, that is to say, a cartridge or a biochip. Normally a chip is a disposable unit meant for single use.

In a preferred embodiment, the first and second electrodes are positioned at opposing sides of the sample chamber.

In an embodiment of the invention, the biological particles are collected from the gaseous sample while the gaseous sample is flowing through the sample chamber. In another embodiment, the biological particles are collected from the gaseous sample while the gaseous sample is recirculated through the sample chamber, i.e. the gaseous sample passes through the sample chamber more than one time, in order to enhance the capture efficiency. For example, when recirculated, the gaseous sample may flow through the sample chamber at least 2 times, 3 times, 4 times, 5 times, 10 times, 15 times, 20 times, 30 times, 40 times, 50 times, or 75 times, such as at least 100 times. The gaseous sample may e.g. flow through the sample a number of times in the range of 2-200, such as 2-50 times, 50-100 times or 100-200 times.

In an embodiment of the invention, the gaseous sample is provided in the sample chamber by means of a gas flow. During the collection of biological particles the gas flow typically has a flow rate ranging preferably from about 5-1000 mL/minute.

In an embodiment, the gas flow has been terminated before the biological particles are collected from the gaseous sample.

Normally, at least a part of the gaseous sample in sample chamber is positioned or flows between the first and the second electrode. For example, at least 40% of the volume of the gaseous sample is positioned or flows between the first and the second electrode, such as at least 50, 60, 70, 80, 90, 95, 97.5, 99, 99.5, or 99.9% of the volume of the gaseous sample is positioned or flows between the first and the second electrode, such as at least 100% of the volume of the gaseous sample is positioned or flows between the first and the second electrode.

The electrical field applied between the first and second electrodes are described in further detail below.

In a preferred embodiment of the invention, the collected biological particles of the sample chamber are contacted with a first liquid reagent. It may be preferred that the biological particles are contacted while they are still located between the first and the second electrode.

The first liquid reagent may comprise one or more reagents selected form the group consisting of a primer, a nucleic acid, a nucleotide triphosphate and a nucleic acid polymerase.

The first liquid reagent may furthermore comprise additives such as 2-mercaptoethanol, e.g. in a concentration of 10 mM, BSA e.g. in a concentration of 1 mg/ml and/or a detergent e.g. in a concentration of 0.5% to 6% (w/v). The detergent can be selected from the group consisting of Triton X-100, Triton X-114, NP-40, Tween20, Tween80 and similar non-ionic detergents.

The first liquid reagent may furthermore comprise a 5'-3' exonuclease degradable, oligo-nucleic acid probe, the degradation of said nucleic acid probe resulting in release of a redox active component.

The redox active component may e.g. be a metallocene such as e.g. ferrocene.

According to the present invention, the term "nucleic acid", "nucleic acid sequence" or "nucleic acid molecule" should be interpreted broadly and may for example comprise an oligomer or polymer of ribonucleic acid (RNA) or deoxyribonucleic acid (DNA) or mimetics thereof. This term includes molecules comprising naturally-occurring nucleobases, sugars and covalent internucleoside (backbone) linkages as well as molecules having non-naturally occurring nucleobases, sugars and covalent internucleoside (backbone) linkages which function similarly or combinations thereof. Such modified or substituted nucleic acids may be preferred over native forms because of desirable properties such as, for example, enhanced affinity for target nucleic acid molecule and increased stability in the presence of nucleases and other enzymes, and are in the present context described by the terms "nucleic acid analogues" or "nucleic acid mimics". Preferred examples of nucleic acid mimics are peptide nucleic acid (PNA-), Locked Nucleic Acid (LNA-), xylo-LNA-, phosphorothioate-, 2'-methoxy-, 2'-methoxyethoxy-, morpholino- and phosphoramidate-comprising molecules or functionally similar nucleic acid derivatives.

According to the present invention the term "primer" relates to a nucleic acid molecule, which typically comprises in the range 5-100 nucleotides, such as 5-20, 20-50 and 50-100 nucleotides. In a preferred embodiment a primer comprises in the range 5-40 nucleotides, such as 5-10, 10-20, 20-30 and 30-40 nucleotides.

The term "nucleic acid polymerase" relates to a DNA- or RNA-dependent DNA polymerase enzyme that preferably is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from thermophilic or caldoactive strains such as *Thermus flavus, T. ruber, T. thermophilus, T. aquaticus, T. lacteus, T. rubens, Thermococcus litoralis, Pyrococcus furiosus, Bacillus stearothermophilus* and *Methanothermus fervidus*. Nonetheless, polymerases that are not thermostable also can be employed in nucleic acid amplification provided the enzyme is replenished.

The further analysis to which the collected biological particles may be subjected could for example involve a pretreatment step such as extraction of biological materials. In a preferred embodiment of the invention, the extraction of biological particles is performed according to co-pending patent application "Method, chip, device and system for extraction of biological material", PCT Application No. PCT/DK2005/000132 (WO2005/083078 A1), which is incorporated herein by reference. As described in PCT Application No. PCT/DK2005/000132 (WO2005/083078 A1), the biological materials such as genetic material may be extracted from the biological particles by contacting the biological particles with a liquid, e.g. the first liquid reagent, and then expose the biological particles to an alternating electric field. The alternating electric field ruptures most biological particles and may even rupture bacterial spores, thus releasing biological material from the biological particles for further analysis.

The further analysis of the released biological material may also include processes such as ELISA, protein separation, protein purification. For released genetic material, the further analysis may include incubation with restriction enzymes, nucleic acid amplification such as the PCR process, electrophoresis, and detection, such as, e.g., fluorescence detection or electrochemical detection. The PCR process and the detection may e.g. be performed according to the methods and using the kits described in the co-pending PCT Application No. PCT/DK2005/000131 (WO2005/083114 A1), having the title "Method, kit and system for enhanced nested PCR", which is incorporated herein by reference.

In an embodiment of the invention, the first and/or the second electrodes have a substantial form selected from the group consisting of a sheet, a plate, a disc, a wire, a rod, or any combination thereof. It is presently preferred that at least one electrode has a sheet form and it is even more preferred that both the first and the second electrode have sheet-forms.

In an embodiment of the invention, the first and a second electrode are separated by a distance being at the most 20 mm, preferably being at the most 20 mm, such as at most 15 mm, 10 mm, 9 mm, 8 mm, 7 mm, 6 mm, 5 mm, or at most 4 mm, more preferably being at the most 3 mm, and even more preferably at most 0.5 mm such as at most 0.3 mm, 0.2 mm, 0.1 mm, such as at most 0.05 mm.

For example the first and the second electrode may be separated by a distance in the range of 0.05-20 mm, such as in the range of 0.05-0.1, 0.1-0.2, 0.2-0.3, 0.3-0.4, 0.4-0.5, 0.5-1, 1-2, 2-5, 5-10, or 10-15 mm, such as in the range of 15-20 mm.

Typically the first and the second electrode may be separated by a distance, which is at least 0.02 mm such as at least 0.03 mm or 0.05 mm.

In the present context the term "biological particle" is related to a particle comprising e.g. a microorganism and/or a virus and/or a fragment thereof.

The microorganism may e.g. be selected from the group consisting of an archeal microorganism, a eubacterial microorganism or a eukaryotic microorganism.

E.g., the microorganism may be selected from the group consisting of a bacterium, a bacterial spore, a virus, a fungus, and a fungal spore.

In a preferred embodiment of the invention, the microorganism is an airborne microorganism.

The biological particle may also comprise a plant spore or a fragment thereof.

In a preferred embodiment of the invention, the microorganism is a bacterial spore.

For example, the bacterial spore may be formed by a bacterium selected from the genus *Bacillus* and/or the genus *Clostridium*.

In a preferred embodiment of the invention, the bacterial spore is a spore formed by *Bacillus anthracis*. The biological particle may e.g. comprise a bacterial spore formed by *Bacillus anthracis*. Also, the biological particle may essentially consist of one or more bacterial spores formed by *Bacillus anthracis.*

Another aspect of the present invention relates to a chip for collection of biological particles, the chip comprising a sample chamber comprising:

- a sample chamber with a first opening in fluid connection with the surrounding air and a second opening to form a fluid connection with a device, the sample chamber comprising an gaseous sample,
- a first and a second electrode positioned at opposing sides of the sample chamber.

In a preferred embodiment of the invention, the chip furthermore comprises a biological particle attached to the first or the second electrode.

In another embodiment of the invention, the potentials of the first and the second electrode are selected so at yield a capture efficiency of at least 50% for biological particles having an effective length in the interval from 1-10 micrometer.

In yet an embodiment of the invention, the electric field of the first and the second electrode are selected so at yield a capture efficiency of at least 50% for biological particles having an effective length in the interval from 1-10 micrometer.

The electric field magnitude may be chosen from the group of: 50 V/mm, 100 V/mm, 200 V/mm, 300 V/mm, 400 V/mm, 500 V/mm, 600 V/mm, 700 V/mm, 800 V/mm, 900 V/mm, 1000 V/mm, 1100 V/mm, 1200 V/mm, 1300 V/mm, 1400 V/mm, 1500 V/mm, 1600 V/mm, 1700 V/mm, 1800 V/mm, 1900 V/mm, 2000 V/mm.

For example the electric field magnitude may be in the range of 50-2000 V/mm, such as in the range of 50-100, 100-200, 200-300, 300-400, 400-500, 500-750, 750-1000, 1000-1200 V/mm, 1200-1500 V/mm, such as in the range of 1500-2000 V/mm.

In a preferred embodiment of the invention, the first and second electrodes are respectively negatively charged and positively charged, or vice versa. For example, if the potential difference between the two electrodes is 400 V, the negatively charged electrode may have a potential of −200 V relative to ground and the positively charged electrode may have a potential of 200 V relative to ground.

Preferably the electric field is the theoretical electric field, i.e. the potential difference between the first and the second electrode divided with the smallest distances between the first and the second electrode.

The capture efficiency of the sample chamber or of a chip comprising the sample chamber is dependent on the design of and the distance between the first and the second electrode, the structure and materials of the sample chamber and the potentials applied to the first and the second electrode.

In a highly preferred embodiment of the invention, the first potential of the first electrode and the second potential of the second electrode, and thus the electric field between the first and the second electrode, are selected so as to yield a capture efficiency of at least 50% for biological particles having an effective length in the interval from 1-10 micrometer, such as a capture efficiency of at least 70%, preferably at least 80%, and more preferably at least 90%, such as at least 95%, 97.5%, 99%, 99.5% or 99.9% such as approximately 100%.

Preferably, the capture efficiency is determined according to the standardised method of Example 4.

According to the present invention, the term "effective length" of a particle is the aerodynamic diameter of the particle e.g. as measures by laser light scattering (O'Brien et al 1986). The aerodynamic diameter of a particle, $d_{pa}$, may be estimated by the formula $$d_{pa}=d_{ps}\cdot\sqrt{\rho_p},$$

where $d_{ps}$ is Stoke diameter in μm and $\rho_p$ is the particle density in g/cm$^3$.

The chip of the present invention comprises a sample chamber comprising a first opening.

The first opening may be used for introducing sample in to the sample chamber. The first opening may be in fluid connection with a sample, e.g. the surrounding air. Alternatively, the first opening is connected to one or more valve(s), which valve(s) may be opened to bring the sample chamber in fluid connection with the sample.

In an important embodiment of the invention, the sample chamber, e.g. the sample chamber of the chip, comprises a second opening. The second opening may e.g. be use for facilitating the introduction of new sample into the sample chamber by allowing air or sample of the sample chamber to escape. The second opening may also be used for introducing a first liquid reagent into the sample chamber. Alternatively the first liquid reagent may enter the sample chamber via the first opening.

The sample chamber, e.g. the sample chamber of the chip, is typically a microscale sample chamber. In an embodiment of the invention, the volume of the sample chamber is at most 500 μL such as at most 400 μL, 300 μL, 200 μL, 100 μL, 50 μL, 25 μL, 15 μL, 10 μL, 5 μL, 4 μL, 3 μL, or at most 2 μL, such as at most 1 μL. For example, the volume of the sample chamber may be at most 500 nL such as at most 400 nL, 300 nL, 200 nL, 100 nL, 50 nL, 25 nL, 15 nL, 10 nL, 5 nL, 4 nL, 3 nL, or at most 2 nL, such as at most 1 nL.

Typically, the volume of the sample chamber is at least 10 nL. In a preferred embodiment of the invention, the volume of the sample chamber is in the range of 1 μL-50 μL, such as 5 μL-30 μL.

In an embodiment of the invention, the smallest distance between a pair of opposing walls is at most 20 mm, such as at most 15 mm, 10 mm, 8 mm, 6 mm, 4 mm, 3 mm, or 2 mm, such as at most 1 mm. For example, the smallest distance between a pair of opposing walls is at most 800 μm such as at most 600 μm, 500 μm, 400 μm, 300 μm, 200 μm, 100 μm, 50 μm, 25 μm, 15 μm, 10 μm, 5 μm, 4 μm, 3 μm, or at most 2 μm, such as at most 1 μm.

Typically, the smallest distance between a pair of opposing walls is at least 5 μm. In a preferred embodiment of the invention, the smallest distance between a pair of opposing walls is the range of 50 μm-500 μm, such as 100 μm-400 μm, and 150 μm-350 μm.

In an embodiment of the invention, the length of the sample chamber, e.g. the sample chamber of the chip, is in the range of 1 mm-50 mm, such is in the range of 1 mm-10 mm, 10 mm-20 mm, 20 mm-30 mm, 30 mm-40 mm, or 40 mm-50 mm. In a preferred embodiment the length of the sample chamber is in the range of 2 mm-8 mm, such as 3 mm-7 mm or 4 mm-6 mm. For example, the length of the sample chamber may be about 4.5 mm.

In an embodiment of the invention, the width of the sample chamber, e.g. the sample chamber of the chip, is in the range of 0.2 mm-10 mm, such is in the range of 0.2 mm-1 mm, 1 mm-3 mm, 3 mm-5 mm, 5 mm-7 mm, or 7 mm-10 mm. In a preferred embodiment the width of the sample chamber is in the range of 0.2 mm-2 mm, such as 0.5 mm-1.5 mm and 0.75 mm-1.25 mm. For example, the width of the sample chamber may be about 1 mm.

In an embodiment of the invention, the height of the sample chamber, e.g. the sample chamber of the chip, is in the range of 50 μm-2 mm, such is in the range of 100 μm-1 mm, 200 μm-900 μm, 300 μm-800 μm, 500 μm-700 μm. In a preferred embodiment the height of the sample chamber is in the range of 100 μm-400 μm, such as 200 μm-300 μm.

In an embodiment of the invention, the length of the sample chamber, e.g. the sample chamber of the chip is approximately 4.5 mm, the width of the sample chamber is approximately 1 mm and the height of the sample chamber is approximately 300 μm.

In an embodiment of the present invention the chip furthermore comprises a first and a second electrode.

The first and/or the second electrode may have different shapes or dimensions. For example, the first and/or the second electrode may have a substantial form chosen from the group of a sheet, a plate, a disc, a wire, a rod; or any combination thereof.

In a preferred embodiment of the present invention, the first and the second electrode may e.g. be sheet-like electrodes.

In a preferred embodiment of the present invention the first electrode and the second electrode are facing each other. For example, they may be positioned at opposite sides of the sample chamber.

The first electrode and/or the second electrode may e.g. be positioned inside the sample chamber, standing free in the sample chamber or attached to one or more of the wall of the sample chamber.

The first and/or the second electrode(s) may be embedded in the sample chamber wall(s). For example, the first and the second electrode(s) may be embedded in the sample chamber walls. Alternatively, the first and/or the second electrode(s) may be positioned at the outer surface(s) of the chip.

Preferably the first electrode and the second electrode are positioned at opposite sides of the sample chamber.

The potential difference between the first and second electrode may be in a range that causes particles of uniform or dissimilar sizes to be captured onto a surface or deflected in a given direction that can accommodate a selection or capture of the particles of interest. An electrode, e.g. the first electrode and/or the second electrode may be formed in a number of different materials. Typically, the electrodes are formed in metals or alloys. The first and the second electrode may for example comprise a metal selected from the group consisting of silver, gold, platinum, copper, carbon, iron, graphite, chrome, nickel, cobalt, titanium, mercury or an alloy thereof.

It is also envisioned that an electrode may comprise a conducting liquid and even essentially consist of a conducting liquid. The conducting liquid may e.g. be mercury.

The dimension or/and structure of electrodes typically depend on the dimension and/or structure the sample chamber. The length and width of the electrodes are of the same order of magnitude as the length and width of the sample chamber.

The electrodes can be formed by as little as a coating of a few atom layers of conductive material.

In an embodiment of the invention, an electrode, e.g. the first and/or the second electrode, has a thickness in the range of 0.001 μm-2000 μm, such as 0.001 μm-1 μm, 1 μm-20 μm, 20 μm-200 μm, and 200 μm-2000 μm.

In an embodiment of the invention, the sample chamber of the chip furthermore comprises a set of detection electrodes, e.g. two or three detection electrodes, for the detection of the presence or absence of redox active component, which e.g. may be released from a probe. Two detection electrodes may serve as working electrode and counter electrode, respectively. The set of detection electrodes may furthermore comprise a reference electrode. Typically, the detection electrodes are formed in metals or alloys. The electrodes may for example comprise a material selected from the group consisting of carbon, silver, gold, or platinum. After detection, the electrodes may suffer from film formation on the electrode surface. To permit further detection of digested probe, further sets of detection electrodes can be placed within the sample chamber of the chip.

In an embodiment of the invention, the first and second electrode may be the set of detection electrodes.

In a preferred embodiment of this invention, the chip furthermore comprises a temperature-sensing element, which e.g. could be a thermally sensitive metal-based resistor (a thermistor) with a positive temperature coefficient (PTC) i.e., the thermistor exhibits increasing electrical resistance with increases in environmental temperature and decreasing electrical resistance with decreasing temperature.

The thermistor may e.g. be selected from the group of materials comprising copper, nickel, iron, aluminium, platinum, or alloys hereof.

The thermistor may have different shapes or dimensions. For example, the thermistor may have a substantial form chosen from the group of a sheet, a plate, a disc, a wire, or a rod.

The thermistor may e.g. be a wire-formed electrode.

The heating electrode may have different shapes or dimensions. For example, the heating electrode may have a substantial form chosen from the group of a sheet, a plate, a disc, a wire, or a rod.

In a preferred embodiment of the present invention, the heating electrode may e.g. be a sheet-like electrode. In a preferred embodiment of the present invention the heating electrode may be positioned to enable heating from at least one side of the reaction chamber.

In yet another embodiment, one or more supplementary heating electrodes may be positioned on the opposing sides of the reaction chamber.

The heating electrode is made of electrically conductive material, preferably selected from the group of nickel-chrome (NiCr), iron-chrome-aluminium (FeCrAl), iron-nickel-chrome (FeNiCr) or other heating element alloys.

In a preferred embodiment of the invention, the chip comprises one or more conducting contact pads in electrical contact with the electrodes of the chip. The chip may comprise a conducting contact pad in electrical contact with the first electrode. The chip may comprise a conducting contact pad in electrical contact with the second electrode. The chip may comprise two conducting contact pads in electrical contact with each their end of the heating electrode. The chip may comprise two or three conducting contact pads in electrical contact with each their electrode of the set of detection electrodes.

Figure 11:
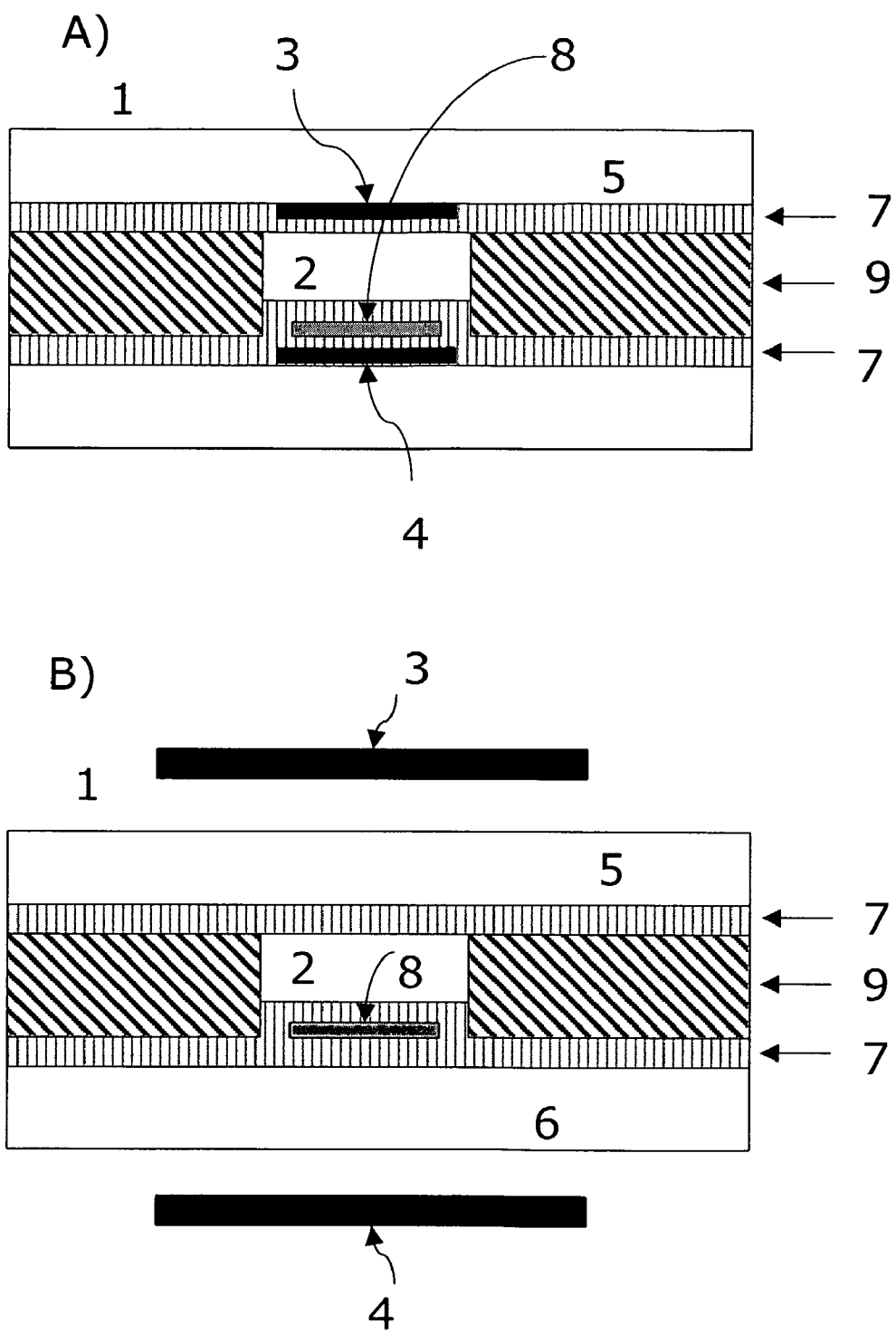
FIG. 11 shows two embodiments of a chip.

In FIG. 11, two exemplary chip embodiments are illustrated. In FIG. 11A) the chip (1) comprises the sample chamber (2) and a first electrode (3) and second electrode (4). The first electrode (3) is attached to the upper part (5) of the chip and the second electrode (4) is attached to the lower part (6) of the chip. Both the first and second electrodes are covered by an electrically insulating layer (7) to prevent unwanted electrolysis of the liquid contents of the sample chamber (2). A heating electrode is embedded in the insulating layer on top of the second electrode. The sample chamber is formed via a spacer part (9), which is sandwiched between the first part (5) and the second part (6) of the chip (1). The set of detection electrodes and the temperature sensing element are not shown in FIG. 11.

Further embodiments of the chip and the sample chamber as shown in FIGS. 1-8.

The chip may comprise a vast array of different materials. It may for example comprise organic polymers such as plastics, metals and semiconductors such as silicon, glasses and ceramics and so fort.

With respect to FIG. 11, the first and second parts could e.g. comprise materials such as plastics, semiconductors such as silicon, glasses or ceramics. The first and second electrode could e.g. comprise a metal such as gold or copper. The insulating layer could e.g. be a film of $SiO_2$ or polyimide. The heating electrode could e.g. be a NiCr electrode and the spacer layer might e.g. be cast a polydimethylsiloxane (PDMS) elastomer.

In FIG. 11B) the first and second electrode are not comprised by the chip but may e.g. be comprised by a device for operating the chip.

The chip may comprise just a single sample chamber or it may comprise multiple sample chambers.

A chip typically has a thickness in the range of 0.5 mm-50 mm, and preferably in the range of 2 mm-8 mm.

A chip typically has a length or diameter in the range of 10 mm-500 mm, preferably in the range of 40 mm-200 mm.

A chip typically has a width in the range of 5 mm-200 mm, preferably in the range of 20 mm-100 mm.

A further aspect of the invention relates to a device for collecting biological particles in a chip. The device may for example be an air-sampling device or a device for collecting biological particles from a gaseous sample. The device preferably comprises:
 a chip site where the chip is to be located in order be functionally associated with the device, and
 a programmable unit comprising a software that effects that the device performs one or more actions selected from the group consisting of:
  applying an first potential to the first electrode and a second potential to the second electrode, thus resulting in a potential difference and an electric field between the first and second electrode, to assist electrostatic collection, in the sample chamber, of a biological particle from the gaseous sample,
  contacting collected biological particles in the sample chamber with a first liquid reagent, and
  performing further analysis of the collected biological particles.

In the present context the term "functionally associated" means that the chip is associated with the device, so that the device can perform one or more actions affecting the chip.

In an embodiment of the invention, the chip is functionally associated with the device when the device can affect the electric field of the contents of the sample chamber.

In an embodiment of the invention, the chip is functionally associated with the device when the device can control the potential of at least one electrode of the chip. For example, the device may be functionally associated with the chip when the device can control the potential of the first electrode and/or the second electrode of the chip.

Being functionally associated may furthermore include that the sample chamber of the chip is in fluid communication with a flow controlling means.

In an embodiment of the invention, the device comprises the first and second electrode, and when the chip is functionally associated the electrical field between the first and second electrode assist collecting the biological particles of the gaseous sample in the sample chamber. In this embodiment, the chip need not comprise the first and second electrode.

The device may furthermore comprise an electrical power supply for supplying power, e.g. to the flow generating means, and/or to the programmable unit, the first and second electrodes.

In an embodiment of the present invention, the chip is functionally associated with the device via the chip site. The chip site may e.g. comprise a plastic interface serving both as connecting material and as gaskets ensuring tight junctions between chip-ports and device-ports eliminate leakage of air and liquid. The chip site may for example comprise a surface and/or cradle for receiving the chip. Typically the chip site comprises at least one conducting contact pad. Preferably, the chip site comprises at least a conducting contact pad for providing electrical contact with the first electrode of the chip and a conducting contact pad for providing electrical contact with the second electrode of the chip.

The programmable unit contains instructions, preferably computer readable e.g. software, adapted to facilitate controlling, monitoring, and/or manipulating of the device prior to operation, under operation, and/or after operation.

The programmable unit preferably comprises at least one computer having one or more computer programs stored within data storage means associated therewith, the computer system being adapted to for controlling the device. The programmable unit may in the context of the present invention be chosen from the non-exhaustive group of: a general purpose computer, a personal computer (PC), a programmable logic control (PLC) unit, unit, a soft programmable logic control (soft-PLC) unit, a hard programmable logic control (hard-PLC) unit, an industrial personal computer, or a dedicated microprocessor.

The present invention also relates to a computer program product being adapted to enable a computer system comprising at least one computer having data storage means associated therewith to control, monitor, and/or manipulate the device prior to operation, under operation, and/or after operation. The present invention further relates to a computer readable medium having stored therein a set of routines for enabling a computer system comprising at least one computer having data storage means associated therewith to control, monitor, and/or manipulate the device prior to operation, under operation, and/or after operation.

The programmable unit for controlling, monitoring, and/or manipulating the device prior to operation, under operation, and/or after operation preferably is preferably adapted for operation under harsh conditions, such as arctic climate, tropical climate, and combat environment, in particular combat zones having being subjected to atomic, biological, and/or chemical warfare (ABC-warfare). Preferably, the programmable unit complies with the relevant military specifications for such units.

In an embodiment of the invention, the programmable unit comprising the software furthermore effects that the device checks if the chip is functionally associated with the device.

The programmable unit comprising the software may furthermore effect that the device performs one or more actions, such as e.g. 2, 3, or 4 actions, selected from the group consisting of
providing a gaseous sample in sample chamber,
applying an first potential to the first electrode and a second potential to the second electrode, thus resulting in a potential difference and an electric field between the first and second electrode, to assist electrostatic collection, in the sample chamber, of a biological particle from the gaseous sample,
contacting the collected biological particle with a first liquid reagent,
performing a further analysis.

The programmable unit comprising the software may e.g. effect that the device provides a gaseous sample in sample chamber by operating a flow generating means for providing a gaseous sample.

The programmable unit comprising the software may e.g. effect that the device applies a first potential to the first electrode and a second potential to the second electrode.

The programmable unit comprising the software may e.g. effect that the device contacts the collected biological particle with a first liquid reagent by operating a flow generating means for providing liquid reagent and/or operating the means for controlling a flow.

The programmable unit comprising the software may effect that the collected biological particles contacted with the first liquid reagent are subjected to further analysis, e.g. by effecting that the device exposes the reaction mixture to an alternating electric field in said sample chamber by modulating the potentials of at least two electrodes, e.g. the first and the second electrode as described herein or another set of electrodes dedicated to the alternating electric field.

The programmable unit comprising the software may effect that the collected biological particles contacted with the first liquid reagent are subjected to further analysis, e.g. by effecting that the device performs a nucleic acid amplification of a target nucleic acid sequence by operating a heating electrode as described herein.

The programmable unit comprising the software may effect that the collected biological particles contacted with the first liquid reagent are subjected to further analysis, e.g. by effecting that the device measures the presence of the amplified target nucleic acid sequence and/or measuring products resulting from amplification of the target nucleic acid sequence by operating the detection electrodes related to differential pulse voltammetry.

In a preferred embodiment of the invention, the device furthermore comprises an electrical interface between the device and the chip for applying an electrostatic field between the first and the electrodes of the sample chamber.

The device may additionally measure a reference signal, i.e. a signal from a sample that either comprising a sample without a biological particle or comprises a well defined amount of a given biological particle. The reference signal may e.g. be retrieved from another chamber remote to the sampling chamber, e.g. a chamber located at another position of the chip, or a chamber located at another chip.

The device may furthermore comprise an internal power supply. The internal power supply may e.g. comprise a battery. The amount of energy to be utilized during a PCR reaction can be estimated as the amount of heat required to heat a volume of water equivalent to that of the fluid sample between the minimum and maximum temperatures of the PCR cycle. This temperature difference is approximately 50 K, and so the heat to be transferred per cycle is approximately 6 Joules for a 30 μL sample volume. Running for example 60 cycles, the total energy consumption for one PCR reaction amounts to 60*6=360 Joules. Using a ramping time comparable to commercial thermocyclers (i.e. 2° C. per second) the power required is 360*2/50=14.4 W.

The battery voltage is considered to be the rated voltage of the battery, e.g. 1.2V per cell for nickel-cadmium (NiCd) and nickel-metal hydride (NiMH$^+$) batteries and 3.6V per cell for most lithium-ion (Li-ion) batteries. The charge capacity of the battery is typically given in terms of milliAmp-hours (mAh) and is expressed as the C-rating. For example, a load current of 1C for a battery with a C-rating of 1200 mA-hours is 1200 mA. A battery can be viewed as being ideal, (i.e., with a constant energy capacity) when draining with a load current below 0.1C (Linden, D. 1984.). Therefore, when delivering a power output of 14.4 W using e.g. a battery delivering 10.8V, the C-rating of this battery should be in the range of 14.4/(10.8*0.1)=13300 mAh to avoid peak power consumption that will dramatically reduce the energy capacity.

To enable this energy consumption and power delivery, and to further ensure true portability, rechargeable batteries are preferred. In a preferred embodiment of the present invention rechargeable batteries are selected from the group consisting of Nickel Metalhydride (NiMH$^+$) based batteries and Lithium-ion (Li-ion) based batteries.

Also, the internal power supply may comprise a generator, e.g. a portable generator. A portable power generator can be utilized as external power supply. The portable power generator can be recharged from, or simply consist of, a solar module, a battery charger (e.g., AC or car battery charger), a fuel combusting generator, or similar.

Alternatively, power from an external power supply can be provided to the device, e.g. supplemented with a battery back-up.

In an embodiment of the invention, the device furthermore comprises a flow generating means e.g. for providing a gaseous sample in the sample chamber of the chip and being in fluid connection with the second opening of the sample chamber when the chip is inserted in the device.

The flow generating may comprise a pump such as a piston pump, a membrane pump, or a positive displacement pump.

In an embodiment of the present invention, the pump is able to deliver an appropriate gas flow through the chip during sampling (in the range of 10 mL/min to 500 mL/min) is selected. Preferably, the pump should be selected to fulfil one or more of the following criteria: small size, lightweight, pulsation-free flow, reversible flow of the medium by changing motor polarity, flow volume adjustable by controlling voltage.

In an embodiment of the invention, the flow generating means may comprise an inkjet dispenser for creating small droplets of reagent or a similar micro dispensing device.

In one embodiment of the present invention, the gaseous sample can be provided by a passive flow through the chip. This will demand a velocity difference between the chip and the surrounding air to be sampled. The conditions for this occurrence are fulfilled if the chip is moved through the air, e.g. mounted on an airplane in such a way that the first opening is in fluid connection with the surrounding air, optimally opposing the flight direction. Alternatively, the conditions occur if the air is moving around the chip having no velocity compared to the air, e.g. mounted in an air vent.

In an embodiment of the invention, the device furthermore comprises a means for controlling a flow, e.g. a flow through the sample chamber.

The flow may e.g. be a liquid flow and/or a gas flow.

The means for controlling a flow typically comprises one or more valves. The valves may be selected e.g., from the group consisting of a check valve, a two way valve, a multi position valve and a pinch valve.

The valve may e.g. be a microfabricated valve and in an embodiment the valve is integrated in the chip.

In an embodiment of the present invention, the first reagent liquid can be delivered using the Ink-Jet micro dispensing technology. An Ink-Jet cartridge containing one or more compartments comprising the first liquid reagent or separate components of the first liquid reagent is mounted in such a way that it enables the microdispensing of liquids into the reaction chamber.

In yet another embodiment of the present invention, the first liquid reagent or separate components hereof are encapsulated within sealed envelope being composed of a plastic polymer. The plastic polymer envelope is equipped with a build-in heating electrode, enabling the melting of the plastic polymer by the application of an appropriate electrical current and the subsequent release of the encapsulated liquid into the chip. In yet another embodiment, the release of liquid from the sealed plastic polymer envelope can be achieved by mechanical or physical rupturing of the envelope, e.g. by puncturing the envelope with a sharp object.

In one embodiment of this invention, the device can be equipped with a display enabling a visual readout of the results. The display can be in the format of a light emitting source (a LED, a light bulb or similar), a screen, a digital readout or any combinations of the mentioned. In yet another embodiment of this invention, the readout can be communicated in the form of audio signals.

In a preferred embodiment of this invention, the device comprises a component that allows for wireless communication. Examples of wireless communication are 802.11 Mobile Wireless LAN, cellular, Bluetooth®, GPS, and Ultra Wideband. The communication can be one-way, e.g. transport of data from the device or transport of data to the device, or the communication can be the combination, i.e. two-way. Established communication can further be expanded to inter-device communication, i.e., establishment of an ad-hoc network enabling one device to trigger the initiation of sampling of another device thus facilitating the monitoring of, for example, the progression of an aerosol cloud.

In a preferred embodiment of the invention, the device is a low weight and/or portable device.

In an embodiment of the present invention, the device weighs at most 10 kg, such as at most 8 kg, 6 kg, 4 kg, 3 kg, or 2 kg, such as at most 1 kg. It may even be preferred that the device weighs at most 800 g such as at most 600 g, 500 g, 400 g, 300 g, 200 g, 150 g, 100 g, 80 g, 60 g, 50 g, 40 g, 30 g, 20 g, 10 g, or 5 g, such as at most 1 g.

Typically the device has a total weight in the range of 20 g-1 kg, such as 20 g-50 g, 50 g-100 g, 100 g-250 g, 250 g-500 g or 500 g-1000 g.

In a preferred embodiment of the invention, the device furthermore comprises an electrical interface between the device and the chip for applying an electrostatic field between the first and the electrodes of the sample chamber.

In an embodiment of the invention, the device comprises the first and second electrode, and when the chip is functionally associated the electrical field between the first and second electrode assist collecting the biological particles of the gaseous sample in the sample chamber. In this embodiment, the chip needs not to comprise the first and second electrode.

In an embodiment of the invention, the device furthermore comprises a flow generating means e.g. for providing an gaseous sample in the sample chamber of the chip and being in fluid connection with the second opening of the sample chamber when the chip is inserted in the device.

The device may also comprise a first reagent chamber for receiving and/or holding a first liquid reagent. Typically, the first reagent chamber has at least one opening, which are in fluid connection with the sample chamber when the chip is functionally associated with the device. Alternatively, the at least one opening of the first reagent chamber is brought in fluid connection with the sample chamber e.g. by using the means for controlling a flow. The first reagent chamber may also be closed by a removable barrier during storage, said barrier being removed either reversibly or irreversibly when the device is used.

Still a further aspect of the invention relates to a system for collecting biological particles, the system comprising a chip as defined herein functionally associated with a device as defined herein.

In an embodiment of the present invention, the chip and the device of the system are integrated and are not meant to be physically separated from each other. In an embodiment of the invention, the chip and the device of the system are integrated so that they cannot be physically separated from each other without damaging the chip or the device.

In an important embodiment of the present invention, the system is a disposable system, e.g. meant to be used only once.

In another important embodiment the chip of the system is disposable but the device is meant to be reused.

A special aspect of the invention encompasses a method and a microstructure aimed at facilitating the collection and concentration of bioparticles (particles containing or comprising living or non-living microorganisms) from a gaseous sample.

A purpose of the present invention is to perform an efficient and rapid sampling of bioparticles. This purpose is obtained by a method and a structure comprising the combined usage of an electric field induced over the airflow. Said usage consists of a structure encompassing a set of electrodes exerting an electrical field that can be varied in voltage and applied for a variable time, and a set of optimal parameter settings for the said usage The present invention describes a method and a device that enables the application of an electrical field at an angle or perpendicular to the air-flow passing through the device and as a result of this method bioparticles are collected and concentrated within said device.

As shown in the accompanying drawings, the present invention relates to a method, device and system for sampling and concentrating microorganisms in a gaseous sample. Said method and system is enabling the detection of said microorganism by subsequent appropriate means. The detecting step may be carried out in suitable manners, with suitable detecting means, as apparent to a person skilled in the art.

Broadly described, the sampling and concentrating methods according to the present invention is essentially concerned with the trapping or capturing by means of an electrical field applied at an angle or perpendicular to the air-flow circulated through the device.

In a special embodiment of the invention, as shown in the accompanying figures, the device comprises a chamber and two opposite positioned electrodes, preferably plate electrodes. The gaseous sample to be examined is passed through the chamber and, as better shown in FIGS. 7 and 8, the chamber has an inlet for receiving the gaseous sample into the chamber and an outlet for releasing the gaseous sample from the chamber, the gaseous sample circulating through the chamber from the inlet to the outlet thereof. As also shown, the electrodes are positioned within the chamber between the inlet and the outlet, said electrodes having an electrical potential thus allowing the gaseous sample to pass through while capturing microorganisms from it.

Figures 3, 4:
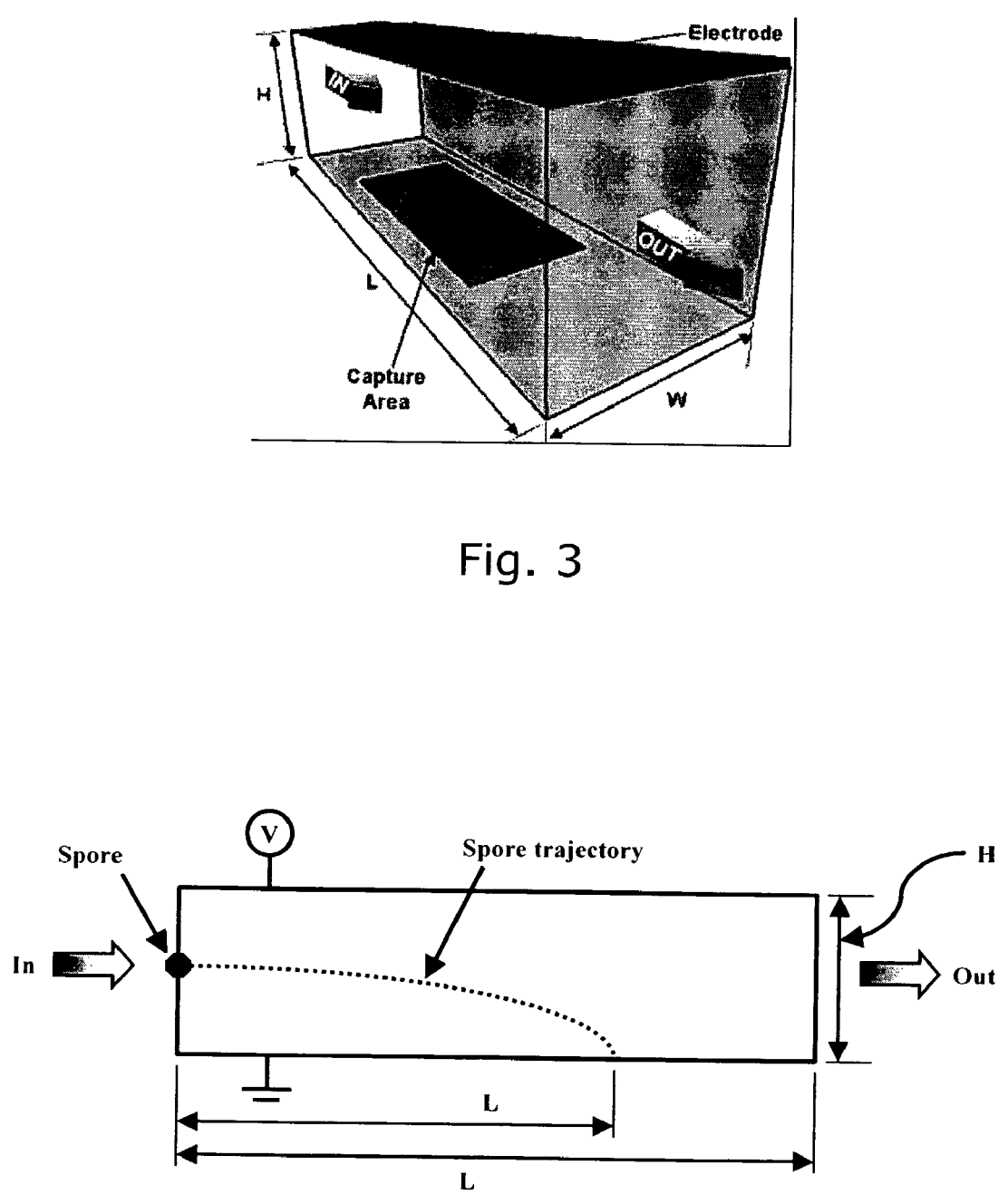

According a special embodiment of the invention, as better shown in FIG. 3 the electrodes consist of an assembly having two plate electrodes positioned perpendicular to the air-flow circulated through the device.

Figure 2:
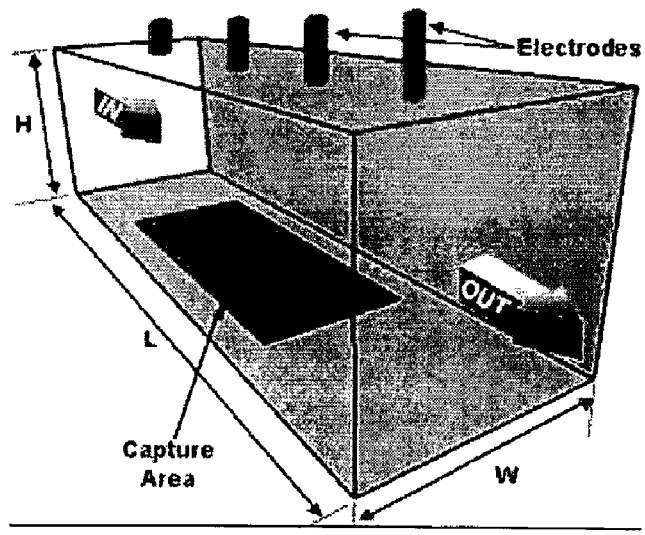
FIG. 2 shows a sample chamber comprising a plate or sheet-like electrode and a wire electrode.
Figure 5:
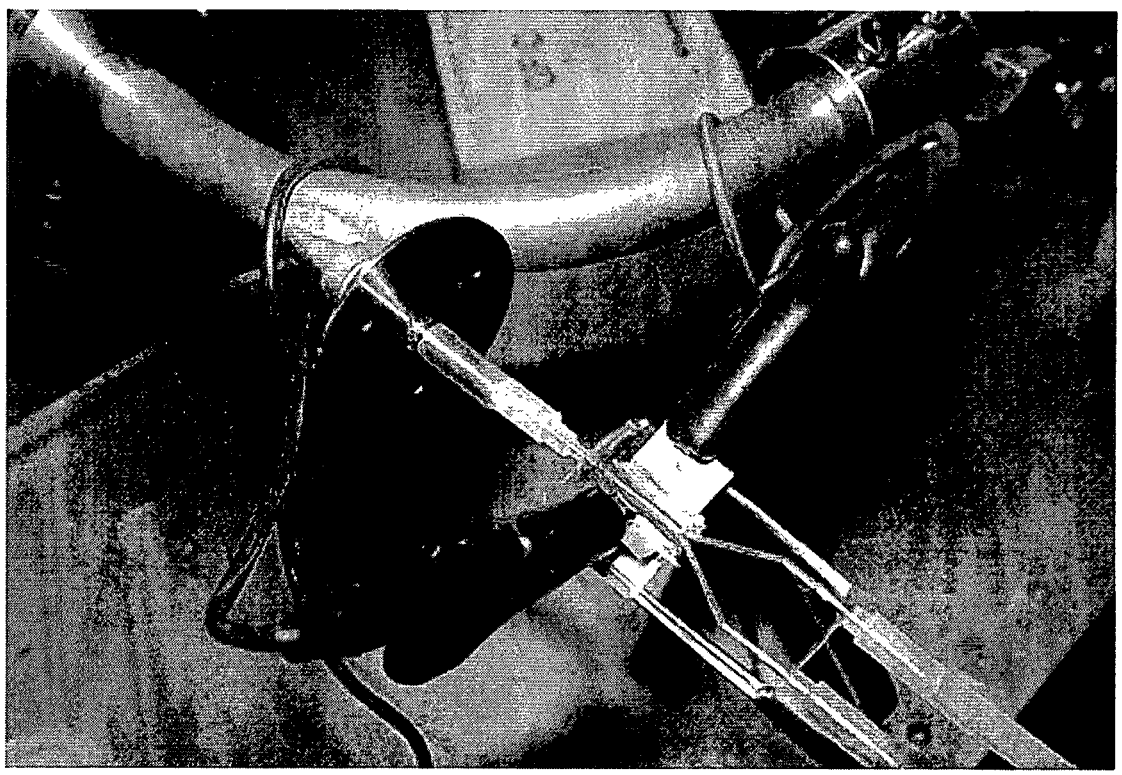
FIG. 5 shows an embodiment of a chip functionally associated with a device.

In another special embodiment of the invention, as better shown in FIG. 2 the electrodes consist of an assembly having a wire electrode and one plate electrode positioned perpendicular to the air-flow circulated through the device.

In a further special embodiment of the invention, as better shown in FIG. 1 the electrodes consist of an assembly having one or more point electrodes and one plate electrode positioned perpendicular to the air-flow circulated through the device.

In either case, according to the present invention, said device is used within a system for detecting the presence of microorganisms in a gaseous sample, taken from either a gaseous environment to be examined, as apparent to a person skilled in the art.

In another special embodiment of the invention, the system and the components thereof are preferably devised to sample and concentrate microorganisms such as bacteria (e.g. *Bacillus* spp., *Clostridium* spp., *Legionella* spp., *E. coli* O157:H7, *Neisseria* spp., *Mycobacterium tuberculosis*), fungi (e.g. *Aspergillus flavus, fumigatus, Niger, Histoplagma capsulatum, Coccidioides imitis*), viruses (e.g. small pox, influenza virus, rubella virus) and the like.

Figure 7:
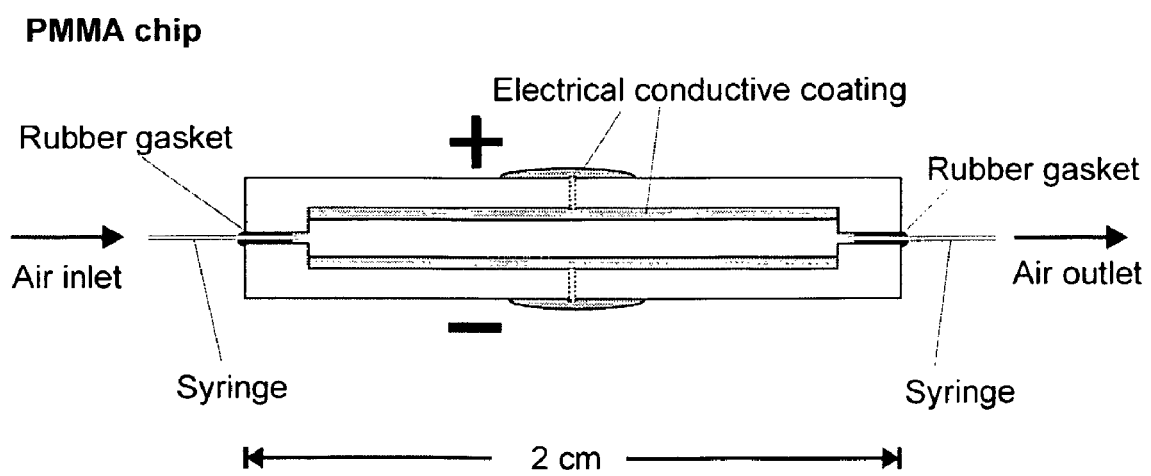
FIG. 7 shows a cross section of an embodiment of a PMMA based chip.
Figure 8:
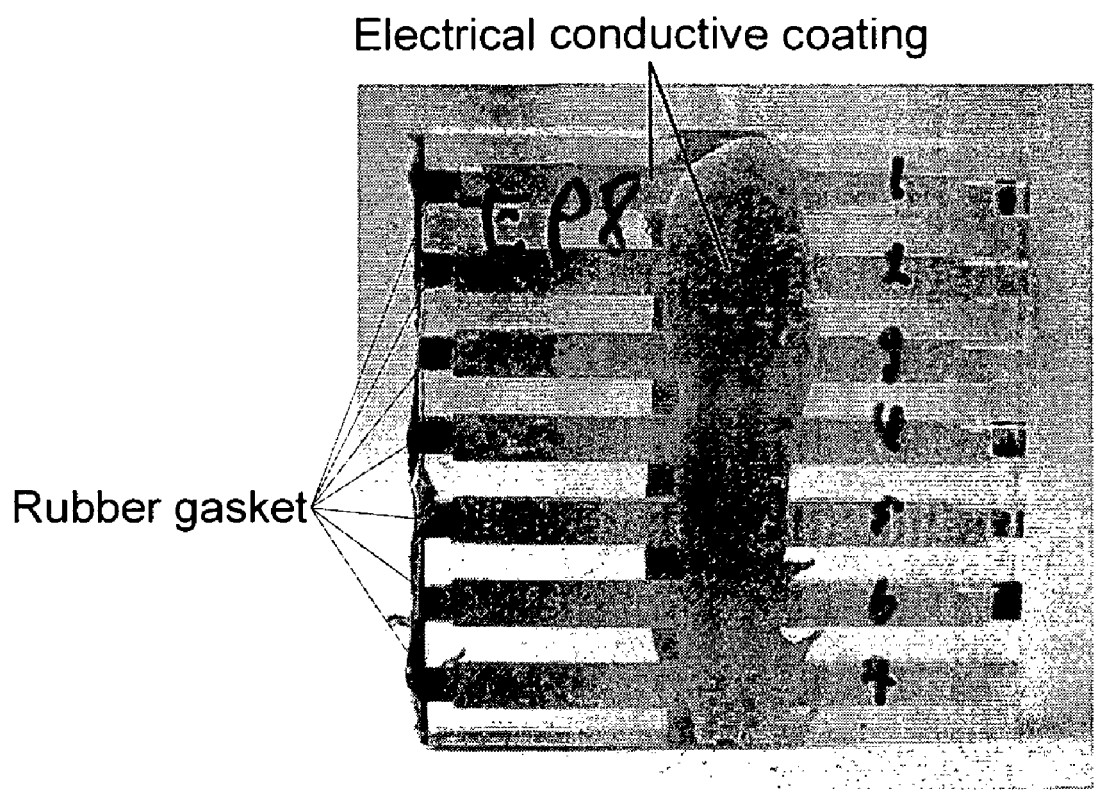
FIG. 8 shows an embodiment of a chip comprising 7 sample chambers.

A special embodiment of the present invention is illustrated in FIG. 3. This figure shows an example of the device acting as an air-monitoring unit. The unit shown in FIG. 3 and exemplified in FIGS. 7 and 8 is particularly useful for sampling and concentrating harmful microorganisms that might be present in the air environment of facilities such as hospitals, schools, industries, houses, public buildings, farms and the like. In operation, the air-sampling device is preferably operatively connected in a continuous manner to sample the air of the corresponding facility to be inspected.

The air-sampling device preferably includes an air inlet, an inlet valve, housing, a power supply, an outlet valve, an air pump, an air outlet, a control circuit board (not shown), relay wires from the different components of the system to the control board, and supports for the housing and other components of the system.

The air-sampling device typically functions as follows: the pump provides a particular aspiration flow rate ranging preferably from about 5-1000 milliliters per minute (ml/min) into the air inlet and then, into the sampling chamber. It is worth mentioning that other suitable flow rates may be used with the present invention, as apparent to a person skilled in the art. Also, the gaseous sample to be examined may originate from a person exhaling a breath sample containing or susceptible to contain microorganisms.

In either case, whether the gaseous sample to be examined comes from a gaseous environment or person exhaling a breath sample containing or susceptible to contain microorganisms, it is directed to the sampling chamber of the device by means of the air inlet. Once microorganisms are sampled and concentrated, a skilled person familiar with diagnostic systems will easily find various arrangements to detect the sampled microorganisms leading to identification of said microorganisms.

Preferably, the device is fabricated from the group of materials consisting of polymers, silica, glass, metals, and ceramics.

As may be appreciated, the present invention is a substantial improvement over the prior art within sampling technologies in that the electrostatic precipitation can be successfully embodied onto a biochip and provides a low-cost, robust and well-controlled means for capture of bioparticles directly from air. As apparent (see FIG. 9), the capture efficiency within the biochip easily approaches 80% and can be pushed higher by increasing the voltage. The continued operation of an electrostatic precipitation biochip (EP-chip) provides a single capture and concentration step, which is a major improvement of state-of-art technology.

Although the present invention was primarily designed for sampling microorganisms in an gaseous sample taken from various environments, as will be easily understood by reading the following description and as apparent to a person skilled in the art. For this reason, the expressions "air", "duct", "ventilation", "air-monitoring unit" and the like should not be taken as to limit the scope of the present invention and include all other kinds of substances with which the present invention may be used and could be useful.

In addition, although the preferred embodiment of the present invention as illustrated in the accompanying drawings comprises various components such as valves, pumps, control circuit board, etc., and although the preferred embodiments of the sampling device/system and corresponding parts of the present invention as shown consist of certain geometrical configurations as explained and illustrated herein, not all of these components and geometries are essential to the invention and thus should not be taken in their restrictive sense, i.e. should not be taken as to limit the scope of the present invention. It is to be understood, as also apparent to a person skilled in the art, that other suitable components, as well as other suitable geometrical configurations may be used for the sampling device/system according to the present invention, as will be briefly explained hereinafter, without departing from the scope of the invention.

While several embodiments of the invention have been described herein, it will be understood that the present invention is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features herein before set forth and falling within the scope of the invention as defined in the appended claims.

The present invention may be used for different purposes or uses. For example, the present invention may be used for detection of living (vegetative) bacteria in the air. The device could be installed in a ventilation duct and switched on for a period of several days or weeks. The bacteria would be captured by the capture electrodes and next detected by subsequent method known to persons skilled in the art.

Also, the present invention could be used for the detection of spores such as *Bacillus anthracis* spores. The device could be installed in a ventilation duct and switched on for a period of several days or weeks. The bacteria would be captured by the capture electrodes and next detected by subsequent method known to persons skilled in the art.

Additionally, the present invention could be used for the sampling of particles of various size using appropriate methods of counting. More particularly, it could be used for the detection of microorganisms in air ducts, ventilation systems, air purifiers, air conditioners and vacuum cleaners, the detection of microorganisms in isolation rooms, pharmaceutical and medical clean rooms, etc.

The present invention could also be used for the detection of living pathogens affecting patients, the device being directly connected to the mask of a ventilator for example.

A special aspect of the present invention relates to a micro scaled device for collecting biological particles comprising;
 an impact collector having an inlet opening providing an airflow capability between the air to be sampled and the impact collector, and an outlet opening providing an airflow capability between the impact collector and the exterior of the impact collector, the outlet or inlet being connected to an air-flow producing means for drawing the gaseous sample through the impact collector from the inlet opening to the outlet opening; said impact collector having a collecting component arranged within the impact collector between the inlet opening and the outlet opening, said collecting component consisting of two or more electrodes positioned in parallel and having the surfaces or at least a part of the surfaces coated with or consisting of material capable of leading an electrical current.

In a special embodiment of the invention, the parallel electrodes enable the generation of an electrical field at an angle or perpendicular to the air-flow passing through the device, facilitating particles present in the sampled air to become charged and thereby being captured by adhering to either the positively or negatively charged electrode.

In a special embodiment of the invention, the electrodes generate an electrical field of a size between 100 V/mm and 1500 V/mm.

In a special embodiment of the invention, the biological particles are rinsed of the device using a rinsing fluid and means for drawing the fluid carrying the biological particles through the micro scaled device.

In a special embodiment of the invention, the step of collecting the fluid carrying the biological particles comprises the step of directing said fluid into a reservoir, such that said fluid can be examined for the presence of biological particles.

It should be noted that, according to the present invention, embodiments and features described in the context of one of the aspects of the present invention also apply to the other aspects of the invention.

EXAMPLES

The following examples are illustrative of the wide range of applicability of the present invention and are not intended to limit its scope. Modifications and variations can be made therein without departing from the spirit and scope of the invention. Although any method and material similar or equivalent to those described herein can be used in the practice for testing of the present invention, the preferred methods and materials are described.

Example 1

Materials and Methods

The GPIB software for controlling the voltage generator (see below) used for capturing spores on-chip in the laboratory setup was specifically developed by RTX Telecom A/S, Nørresundby, Denmark. The particle size analyzer model 3321 from TSI (TSI Inc., Shoreview, Minn., USA) was controlled by the TSI software Aerosol Instrument Manager. The Fenix Laser was controlled using Winmark Pro version 4.0.0 build 3773 (Synrad software, Mukilteo, Wash. USA).

The lasing processes were run at 1200 dpi with a speed of 400 pulses/sec and power intensities in the range of 5-10%. Dependent on the required channel depth, the number of overlapping markings was set to a number in between 1 to 10 (10 gave deep channels, whereas 1 gave a very superficial ablation of 20-30 µm deep). Very deep channels (>800 µm) tend to become concave in shape due to the loss of focus of the laser as the ablation digs into the material. The GPIB controlled high voltage power supply model PS310/1250V-25W was purchased from Stanford Research Systems (Stanford Research Systems, Inc. Sunnyvale, Calif., USA). The power supply was utilized for generating voltages in the range of 100-1200 V.

The voltage and pump control of the EP-chips used in the experiments performed in the 63 $m^3$ stainless steel encapsulated aerosol room were developed by RTX Telecom A/S, Nøorresundby, Denmark. The step-up converter delivered 250 V from four 1.5 V standard AA batteries and supported the air pump with power.

A vacuum pump model DC06/03f from Fürgut (Erich Fürgut, Tannheim, Germany) was utilized to mediate air suction in the EP-chips. The DC06/03f device operated at a voltage of 6 V utilizing 220-330 mA, delivering 1.0 l/min of air against a maximal pressure difference of 180 mbar, and had a total weight of 30 g. The advantages of the pump were following: small size, lightweight, pulsation-free flow, reversible flow of the medium by changing motor polarity, flow volume adjustable by controlling voltage.

The Model 3321 Aerosol Particle Sizer (3321 APS) (TSI Inc., Shoreview, Minn. USA) provides two measurements: aerodynamic size and relative light scattering intensity. It detects particles in the 0.37 to 20 µm range with high resolution sizing from 0.5 to 20 µm in aerodynamic diameter. The instrument measures the aerodynamic size in real time. The instrument was set to an airflow of 5 l/min.

The aerosol chamber utilized for the lab experiments was kindly provided by The Institute of Occupational Health, Copenhagen, Denmark and manufactured by Mikrolab (Mikrolab Aarhus A/S, Højbjerg, Denmark). The 50 liter chamber was made of stainless steel mounted on a rotor arrangement allowing the entire chamber to rotate at a speed of 0-60 rpm. The core chamber could be separated in tree parts (two ends and one cylinder). Both end parts were fastened securely by 5 handles. Before assembly the spore material was positioned in the cylinder. The chamber was open and a pump system could blow air with controlled temperature and humidity through the chamber from the backside of the chamber with exit at the nozzle shown on FIG. 5. The nozzle could be connected to a two-piece metal tubing (see FIG. 5) that split the air stream into two. One part going to a HEPA filtered output and the other and smaller entering the chip. PMMA chip connected to the two-piece metal tubing interfaced to the output nozzle from the aerosol chamber. The metal tube seen as turning to the upper right side of the picture entered a low-pressure tract equipped with two overlapping Whatman qualitative filter papers Grade 2V pore size 8 µm (Whatman International Ltd., Maidstone, Kent UK).

Figure 6:
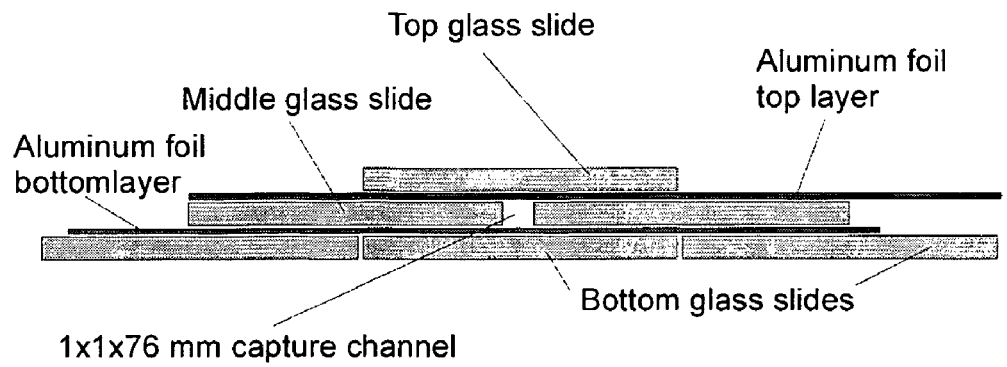
FIG. 6 shows a cross section of an embodiment of glass based chip.

A sample chamber created by microscope slides interfaced to the two-piece metal tubing and connected to the aerosol chambers exit nozzle (see FIG. 6). The interfacing was done by 0.5 mm inner diameter Teflon tubing. The Teflon tubing was glued to the glass by a two component epoxy and hardened overnight. Flow, temperature and humidity control allowing a controlled amount of air at a certain temperature and humidity to enter the aerosol chamber. The air temperature was 26° C. and the humidity was 50%.

The Fenix Laser model 48-2 a 25 watt RF-excited pulsed $CO_2$ laser (Synrad, Inc. Mukilteo, Wash. USA) equipped with a 80 mm lens (lens focal length) with a nominal field of 27×27 cm and a working distance of 74±1 cm. The spot size was 116 µm. A $CO_2$ gas mixture provides an output wavelength at or near 10.6 µm. The Fenix Laser lens system uses a flat field principle giving a high quality and uniformity in the marking process. Rapid Thermo bonding (see below) of the PMMA parts were done at temperatures from 120-200° C. in a BD heating oven (Binder GmbH, Tuttlingen, Germany).

Consumables

PMMA (Poly-methyl-meth-acrylate) plates (Riacryl, RIAS A/S, Roskilde, Denmark) are transparent (>900% transmission), have an excellent UV stability, low water absorption and high abrasion resistance. PMMA has been utilized for making microstructures with laser ablation (Johnson et al 2001) and the material is chemical inert to the ablation process compared with other materials as poly(ethylene-terephthalate-glycol), poly(vinylchloride), and poly(carbonate) (Pugmire et al 2002). The material has furthermore proven suitable to build complicated integrated microfluidic systems characterized as lab-on-chip systems (Johnson et al 2001). The material expresses little joule heating when exposed to electrical fields and can be utilized for DNA separation (Chen & Chen 2000; Sung et al 2001).

Different PMMA designs were made and successfully annealed to each other by rapid thermo bonding at 160-200° C. Alignment was achieved by a prototype alignment tool developed by Mikrolab Aarhus A/S and the alignment was secured by adhesive bonding prior to the rapid thermo bonding by positioning 0.2-0.5 µl cyanoacrylate at the corners of the PMMA plates. It was found that minor amounts of adhesive did not interfere with the thermo bonding process in the vicinity of the active micro structured parts if the adhesive bonding were kept remote to the micro structured sites. The high temperature rapid thermo bonding removed the need for thermo fusion bonding which was seen to damage both alignment and the microstructures themselves.

Electrical conductive coatings were made using Electrodag 1415M containing silver particles in 4-methylpenthan-2-one. The conductive fluid was diluted 1:1 with acetone to reduce the thickness of the coatings.

Example 2

Collection of Spores

Materials

The powder-based *bacillus* spores (Biobit WP, wet-able powder) used in the aerosol-trials contained *Bacillus thuringiensis* subsp. *kurstaki* (Abbott Laboratories, North Chicago, Ill., USA). Based on plating assays of dilution series, the spore concentration of the powder was determined to be 3.2× $10^9$ spores/g (i.e., colony forming units, CFU) with a density of 0.86 g/cm³ (=860 kg/m³).

Particle Analyzer Software

The particle size analyzer model 3321 from TSI Inc., 500 Cardigan Road, Shoreview, Minn. 55126-3996, USA, was controlled by the TSI software Aerosol Instrument Manager Experimental Setup A set of spore capture experiments was performed with a device for electrostatic precipitation having an electrode distance of 1 mm. The flow was recorded to 2 l/min over a 10 minute sampling period and the total particle concentration was estimated to 26 mg/m³ with a geometric mean at 1.53±1.96 µm representing a total of 3304290 particles.

The data from experiments each consists of nine sample periods of 30 seconds each. The three first sample periods are pre-controls showing the stability of the control samples in which the voltage on the electrodes of the device is at 0 Volt. The next three 30 seconds samples are performed with an electrical field of the device set to a capture voltage of 100 to 1200 Volts (from −50V/+50V to −600V/+600V).

The last three 30 seconds sample periods were post-controls, where the voltage on the electrodes of the device is returned to 0 Volt.

The particle counter is counting the particles that are passing through the prototype. Thus, a capture of particles is illustrated by the removal of particles from the population compared to the pre and post controls.

Results

Figure 9:
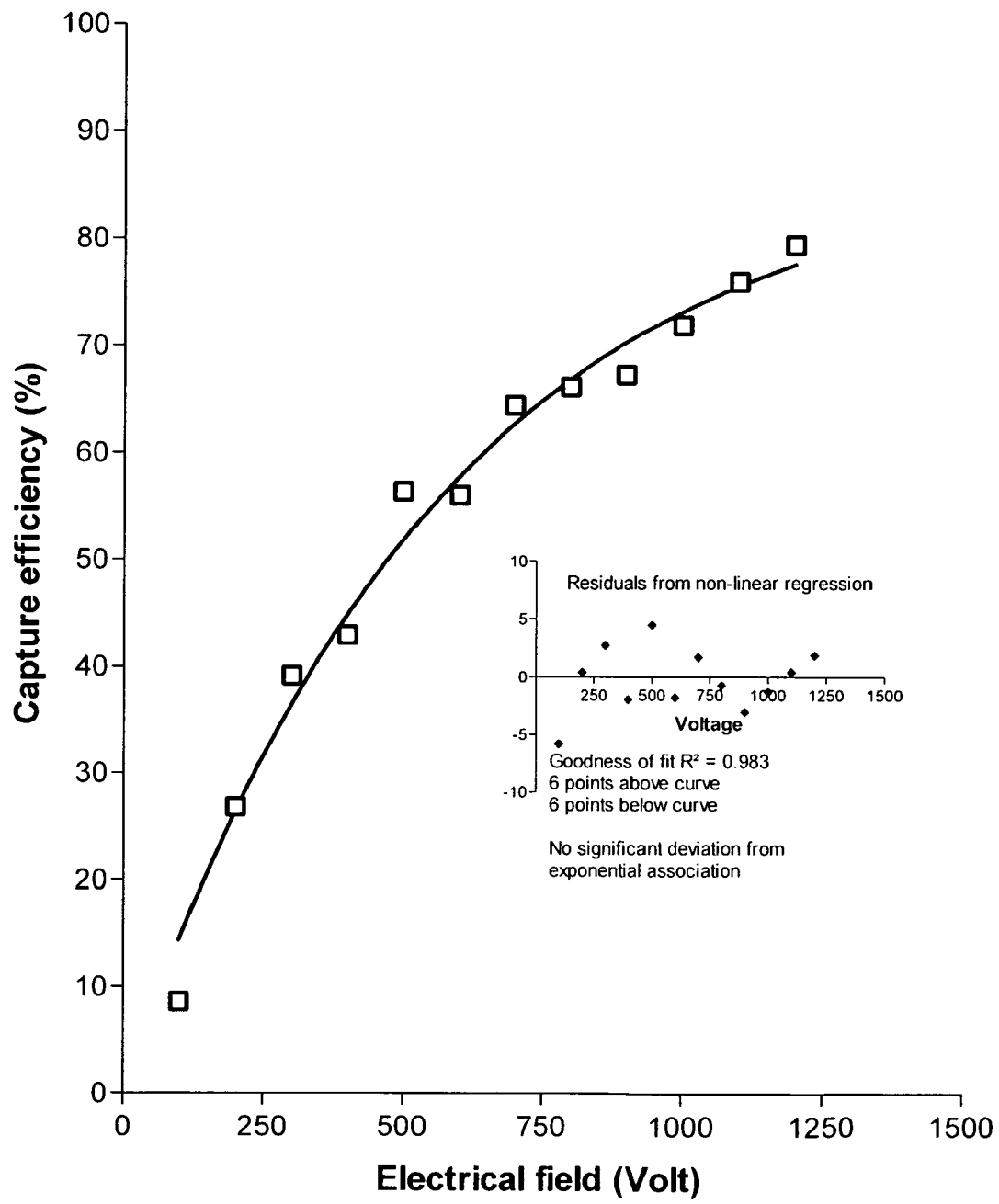
FIG. 9 shows a plot of the capture efficiency as a function of the electric field.

As seen from FIG. 9, the capture efficiency increases with increasing voltage over the electrode.

Figure 10:
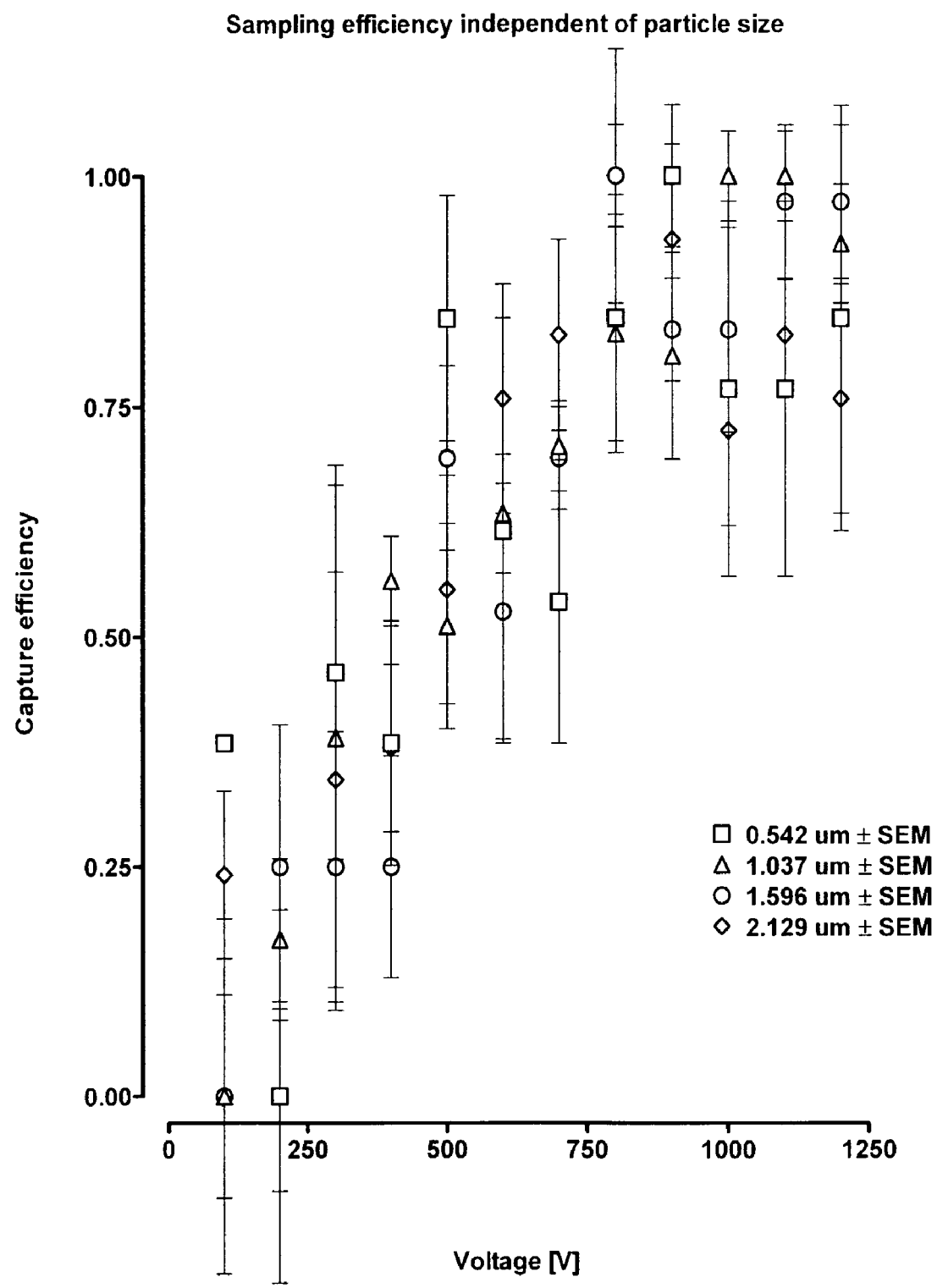
FIG. 10 shows a plot of the capture efficiency independent of particle size.

Taking the sampling efficiencies of the various size fractions and plotting these against the applied voltage over the sampling electrodes, it is seen from the FIG. 10, that there is no significant difference in the capture efficiencies of spores with a geometric mean of 0.542, 1.037, 1.596 or 2.129 µm.

Example 3

Method of Determination of Capture Efficiency

Preparation of Standardized Biological Particles

One hundred mg of Biobit *Bacillus thuringiensis* subsp. *kurstaki* containing approximately $10^9$ spores/g (Valent BioSciences Corp, Libertyville, USA) is resuspended in 1 ml of demineralised water and centrifuged for 90 sec. at 12000 rpm. The supernatant is discarded. This procedure is repeated four times. Prior to the last resuspension, a sample is withdrawn for determination of the number of colony forming units (CFU) per ml. The tube is left for exsiccation in e.g. vacuum until dried.

Dilution series is plated on LB-agar plates (Luria Bertani substrate; 10.0 g tryptone, 5.0 g yeast extract, 10.0 g NaCl, 15.0 g agar resuspended in 1.0 liter H2O–pH=7.0, autoclaved), incubated at 30° C. overnight and inspected for visual colonies. The number of CFU enables the determination of spores in the powder.

Measurement of Capture Efficiency

The washed and dried *Bacillus thuringiensis* spores are aerosolized in an appropriate aerosol chamber resulting in an approximate spore concentration of $10^4$-$10^5$ spores per liter. The chip/sampling chamber for which the capture efficiency is to be determined is connected to the device, thus being functionally associated. Then the chip/sampling chamber is connected to the aerosol chamber and aerosol is aspirated through the sample chamber of the chip with an airflow of approximately 50 mL/minute. A particle counter (e.g. analyzer model 3321 from TSI Inc., 500 Cardigan Road, Shoreview, Minn. 55126-3996, USA) is connected to the outlet of the chip and is counting the number of spores in the size range 1-10 μm that leaves the chip.

First the number of spores of in 25 mL aerosol is measured by aspirating the aerosol while setting the potentials of the first and the second electrode to ground. The measured number of spores is used as the control value, $N_c$.

Then, the selected potentials are applied to the first and the second electrode, another 25 mL aerosol is aspirated through the chip and the number of spores exiting the chip is measured during the aspiration. This value is called $N_s$.

The capture efficiency of the chip/sampling chamber at the selected potentials are calculated as $(N_c-N_s)/N_c*100\%$.

REFERENCES

Mainelis et al 2002a Mainelis G, Gorny R L, Reponen T, Trunov M, Grinshpun S A, Baron P, Yadav J, Willeke K. (2002). Effect of electrical charges and fields on injury and viability of airborne bacteria. *Biotechnol Bioeng.* 79:229-41.

Mainelis et al 2002b Mainelis, G., Adhikari, A., Willeke, K., Lee, S.-A., Reponen, T., and Grinshpun, S. A. (2002) Collection of Airborne Microorganisms by a New Electrostatic Precipitator, *Journal of Aerosol Science,* 33:1417-143

Iversen & Tolo Iversen D B, Tolo K. (1975) Electrostatic air filters for dental practice Nor Tannlaegeforen Tid. 85:446-8

Johnson et al Johnson R D, Badr I H, Barrett G, Lai S, Lu Y, Madou M J, Bachas L G. (2001) Development of a fully integrated analysis system for ions based on ion-selective optodes and centrifugal microfluidics. *Anal Chem.* 73:3940-6.

Pugmire et al 2002 Pugmire D L, Waddell E A, Haasch R, Tarlov M J, Locascio L E. (2002) Surface characterization of laser-ablated polymers used for microfluidics. *Anal Chem.* 74:871-8

Chen & Chen Chen Y H, Chen S H. (2000) Analysis of DNA fragments by microchip electrophoresis fabricated on poly (methyl methacrylate) substrates using a wire-imprinting method. *Electrophoresis.* 21:165-70.

Sung et al Sung W C, Lee G B, Tzeng C C, Chen S H. (2001) Plastic microchip electrophoresis for genetic screening: the analysis of polymerase chain reactions products of fragile X (CGG)n alleles. *Electrophoresis.* 22:1188-93.

O'Brien et al O'Brien D, Baron P, Willeke K. (1986) Size and concentration measurement of an industrial aerosol. *Am Ind Hyg Assoc J.* 47:386-92.

The invention claimed is:

1. A method for collecting or detecting a biological particle from air, the method comprising the steps of:
    a) providing a sample chamber and a first and a second electrode, the first and the second electrode and the sample chamber being so positioned that at least a part of the sample chamber is between the first and the second electrode, and the first and a second electrode is separated by a distance being less than 20 mm, said sample chamber having a volume of at most 500 μL,
    b) providing a gaseous sample in the sample chamber,
    c) applying a first potential to the first electrode and a second potential to the second electrode, thus resulting in a potential difference and an electric field between the first and second electrode, to assist electrostatic collection, in the sample chamber, of a biological particle in the gaseous sample,
    d) contacting the biological particle collected in the sample chamber with a first liquid, and
    e) subjecting the collected biological particle to further analysis.

2. The method according to claim 1, wherein the first potential of the first electrode and the second potential of the second electrode, and thus the electric field between the first and the second electrode, are selected so as to yield a capture efficiency of at least 50% for biological particles having an effective length in the interval from 1-10 micrometer.

3. The method according to claim 1, wherein the first or the second electrodes are from the group of: a sheet, a plate, a disc, a wire, a rod, a point; or any combination thereof.

4. The method according to claim 1, wherein the first and a second electrode are separated by a distance being at the most 10 mm.

5. The method according to claim 1, wherein at least a part of the gaseous sample in the sample chamber is positioned or flows between the first and the second electrode.

6. The method according to claim 1, wherein the biological particle comprises a component selected from the group consisting of a microorganism, a virus, a plant spore, and a fragment thereof.

7. The method according to claim 6, wherein the microorganism is a bacterial spore.

8. The method according to claim 7, wherein the bacterial spore is formed by a bacterium selected from the genus Bacillus or the genus Clostridium.

9. The method according to claim 8, wherein the bacterial spore is a spore formed by Bacillus anthracis.

10. The method according to claim 1, wherein the first and the second electrode are separated by a distance being at the most 3 mm.

11. The method according to claim 1, wherein the sample chamber has a volume of at most 100 μL.

12. The method according to claim 1, wherein the volume of the sample chamber is in the range of 1 μL- 50 μL.

* * * * *